United States Patent
Nackaerts et al.

(10) Patent No.: US 10,518,021 B2
(45) Date of Patent: Dec. 31, 2019

(54) COMPOSITE LIQUID BAG SYSTEM HOLDER

(71) Applicants: Terumo BCT, Inc., Lakewood, CO (US); Andreas Hettich GmbH & Co. KG, Tuttlingen (DE)

(72) Inventors: Kris Nackaerts, Leuven (BE); Makoto Hirabuki, Leuven (BE); Marcellus Geiselmann, Tuttlingen (DE); Bruce Ellingboe, Littleton, CO (US); Hong Duc Nguyen, Denver, CO (US); Timothy M. Taga, Arvada, CO (US); Ross Tichota, Englewood, CO (US); Tadashi Imai, Shizuoka (JP); Armin Brendle, Muehlhausen-Ehingen (DE); Christoph Pabst, Radolfzell (DE); Roland Biset, Hemiksem (BE); Wilfried Mertens, Limburg (BE); Klaus-Günter Eberle, Tuttlingen (DE)

(73) Assignees: Terumo BCT, Inc., Lakewood, CO (US); Andreas Hettich GmbH & Co. KG, Tuttlingen (DE)

( * ) Notice: Subject to any disclaimer, the term of this patent is extended or adjusted under 35 U.S.C. 154(b) by 513 days.

(21) Appl. No.: 15/048,838

(22) Filed: Feb. 19, 2016

(65) Prior Publication Data

US 2016/0243300 A1    Aug. 25, 2016

Related U.S. Application Data

(60) Provisional application No. 62/118,632, filed on Feb. 20, 2015.

(51) Int. Cl.
*B04B 11/04* (2006.01)
*B04B 7/08* (2006.01)
(Continued)

(52) U.S. Cl.
CPC ......... *A61M 1/3693* (2013.01); *B04B 5/0428* (2013.01); *B04B 7/08* (2013.01);
(Continued)

(58) Field of Classification Search
CPC ......... B04B 5/0421; B04B 7/12; B04B 9/146; B04B 11/04; B04B 2011/046; B04B 7/08;
(Continued)

(56) References Cited

U.S. PATENT DOCUMENTS 3,190,546 A * 6/1965 Raccuglia ............. B04B 5/0421
  215/400
6,348,031 B1  2/2002 Unger et al.
(Continued)

FOREIGN PATENT DOCUMENTS

EP    0438520 A1    7/1991
EP    0438520 B1 *  8/1994    ......... G01N 33/5005
(Continued)

OTHER PUBLICATIONS

International Searching Authority, International Preliminary Report on Patentability, dated Aug. 31, 2017, 9 pages.
(Continued)

*Primary Examiner* — Charles Cooley
(74) *Attorney, Agent, or Firm* — Terumo BCT, Inc IP Law Dept.

(57) ABSTRACT

Embodiments of a system box for holding a bag system and methods for separating composite liquids are described. In embodiments, a bag system may be a blood bag system used to collect blood, separate the blood into components, store the components, and utilize the components in patients. The system box may hold the blood bag system. Processes can then be performed to separate components from the blood.

19 Claims, 21 Drawing Sheets

(51) Int. Cl.
    *B04B 5/04*     (2006.01)
    *A61M 1/36*     (2006.01)
    *B04B 11/00*    (2006.01)

(52) U.S. Cl.
    CPC .............. *B04B 11/00* (2013.01); *B04B 11/04* (2013.01); *B04B 2005/0435* (2013.01)

(58) Field of Classification Search
    CPC ............. B04B 11/00; B04B 2005/0435; B04B 5/0428; B01D 21/262; G01N 2035/00504; A61M 1/3693; A61M 1/0209
    USPC ...................................... 494/44, 45
    See application file for complete search history.

(56) References Cited

U.S. PATENT DOCUMENTS

| | | | |
|---|---|---|---|
| 6,740,239 B2 | 5/2004 | Högberg et al. | |
| 6,910,998 B2 * | 6/2005 | Eberle | B04B 5/0428 494/2 |
| 6,994,790 B2 | 2/2006 | Corbin, III et al. | |
| 7,033,512 B2 | 4/2006 | Hlavinka et al. | |
| 7,235,041 B2 | 6/2007 | Högberg et al. | |
| 7,279,107 B2 | 10/2007 | Högberg et al. | |
| 7,347,932 B2 | 3/2008 | Holmes et al. | |
| 7,396,451 B2 | 7/2008 | Holmes et al. | |
| 7,438,679 B2 | 10/2008 | Hlavinka et al. | |
| 7,674,221 B2 | 3/2010 | Hudock et al. | |
| 7,766,809 B2 | 8/2010 | Dolecek et al. | |
| 7,819,793 B2 | 10/2010 | Lindell et al. | |
| 7,833,185 B2 | 11/2010 | Felt et al. | |
| 7,981,019 B2 | 7/2011 | Holmes et al. | |
| 8,016,736 B2 | 9/2011 | Hlavinka et al. | |
| 8,057,377 B2 | 11/2011 | Holmes et al. | |
| 8,120,760 B2 | 2/2012 | Stanton et al. | |
| 8,173,027 B2 | 5/2012 | Högberg et al. | |
| 8,236,184 B2 | 8/2012 | Holmes et al. | |
| 8,277,406 B2 | 10/2012 | Felt et al. | |
| 8,337,380 B2 | 12/2012 | Ellingboe et al. | |
| 8,366,086 B2 | 2/2013 | Bucciaglia et al. | |
| 8,425,448 B2 | 4/2013 | Felt et al. | |
| 8,439,889 B2 | 5/2013 | Sano | |
| 8,460,267 B2 | 6/2013 | Hirabuki | |
| 8,800,881 B2 | 8/2014 | Biset et al. | |
| 8,840,535 B2 | 9/2014 | Dolecek | |
| 8,870,734 B2 * | 10/2014 | Eberle | A61M 1/3693 494/10 |
| 8,900,112 B2 | 12/2014 | Holmes et al. | |
| 8,944,983 B2 | 2/2015 | Nguyen et al. | |
| 8,992,403 B2 | 3/2015 | Eberle et al. | |
| 9,028,388 B2 | 5/2015 | Dolecek et al. | |
| 9,060,920 B2 | 6/2015 | Hirabuki | |
| 9,079,194 B2 | 7/2015 | Hlavinka et al. | |
| 9,132,949 B2 | 9/2015 | Bidet et al. | |
| 9,242,252 B2 | 1/2016 | Eberle et al. | |
| 9,375,729 B2 | 6/2016 | Eberle et al. | |
| 9,579,447 B2 | 2/2017 | Hirabuki et al. | |
| 9,733,805 B2 | 8/2017 | Diaz et al. | |
| 9,820,912 B2 | 11/2017 | Imai | |
| 9,839,729 B2 | 12/2017 | Biset et al. | |
| 9,839,730 B2 | 12/2017 | Biset et al. | |
| 2002/0020680 A1 | 2/2002 | Jorgensen | |
| 2006/0205581 A1 | 9/2006 | Chammas | |
| 2007/0179423 A1 * | 8/2007 | Felt | A61M 1/0209 604/6.01 |
| 2007/0209708 A1 | 9/2007 | Hermann et al. | |
| 2010/0132512 A1 | 6/2010 | Bucciaglia et al. | |
| 2010/0152013 A1 * | 6/2010 | Eberle | B04B 5/0428 494/10 |
| 2011/0003675 A1 | 1/2011 | Dolecek | |
| 2011/0053201 A1 | 3/2011 | Eberle et al. | |
| 2011/0136650 A1 | 6/2011 | Ellingboe et al. | |
| 2011/0294641 A1 | 12/2011 | Dolecek et al. | |
| 2012/0015795 A1 * | 1/2012 | Hlavinka | A61M 1/3693 494/37 |
| 2014/0070122 A1 | 3/2014 | Imai et al. | |
| 2015/0140546 A1 | 5/2015 | James et al. | |
| 2016/0046410 A1 | 2/2016 | Nakamura | |
| 2016/0243300 A1 * | 8/2016 | Nackaerts | B04B 5/0428 |
| 2016/0317727 A1 | 11/2016 | Hirabuki et al. | |
| 2017/0043071 A1 | 2/2017 | Imai | |

FOREIGN PATENT DOCUMENTS

| | | |
|---|---|---|
| JP | 2017169817 A | 9/2017 |
| JP | 2017169982 A | 9/2017 |

OTHER PUBLICATIONS

International Searching Authority, International Search Report, dated May 12, 2016, 3 pages.

* cited by examiner

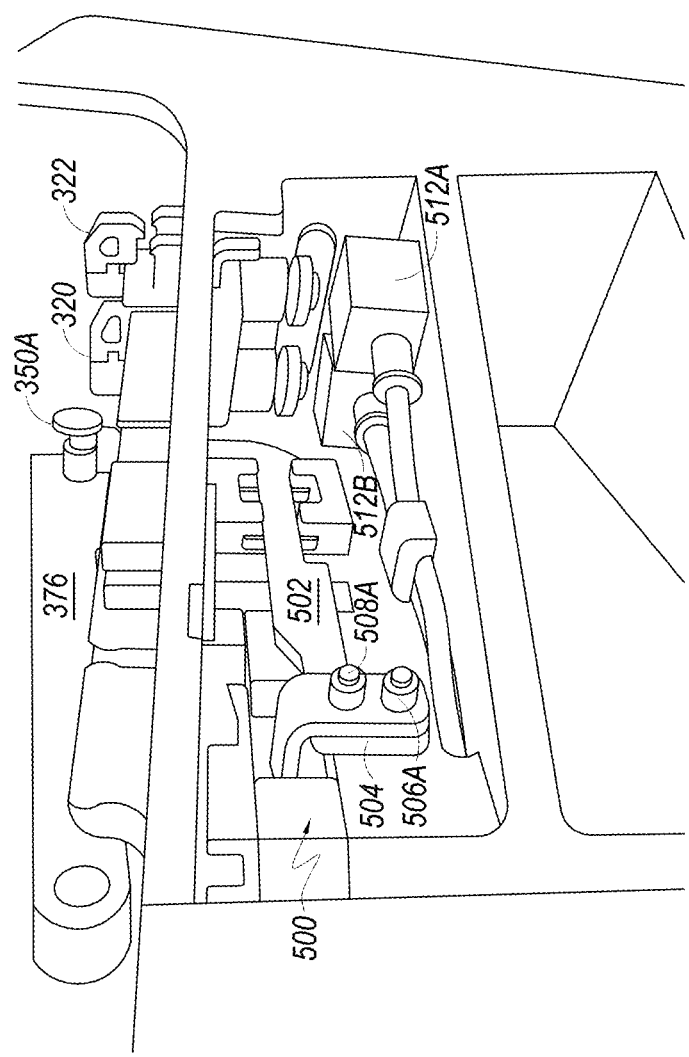

COMPOSITE LIQUID BAG SYSTEM HOLDER

CROSS-REFERENCE TO RELATED APPLICATION(S)

This application claims priority to U.S. Provisional Patent Application No. 62/118,632, filed Feb. 20, 2015, entitled COMPOSITE LIQUID BAG SYSTEM HOLDER, which is hereby incorporated by reference in its entirety as if set forth herein in full.

BACKGROUND

There are many liquids including biological liquids that are separated into components. The components may then be utilized after separation. One example of a biological fluid that is separated into components is whole blood. Conventionally, whole blood obtained by blood donations is separated into its components such as red blood cells, platelets and plasma. The components may then be individually transfused to a patient. It is believed that component transfusion, instead of transfusion of whole blood, may lessen the burden on a patient's circulatory system and reduce possible side effects of transfusion.

Whole blood obtained by blood donation may be centrifuged to separate the whole blood into its components. For example, the whole blood may be separated into a PPP (platelet poor plasma) fraction, a CRC (concentrated red blood cells) fraction, and buffy coat. The buffy coat may contain leukocytes, platelets and red blood cells. Typically, the buffy coat has a large proportion of young fresh platelets.

As noted, whole blood may be separated into blood components including platelet poor plasma, concentrated red cells and buffy coat, which may be stored and transported in separate storage bags. The storage bags may be connected by tubing to create a bag system.

A bag system for storage of blood components may be mounted in a separator device, such as a centrifuge. Depending on the length of tubing, position of bags, and operation of the centrifuge it may be burdensome to position bags and route tubing when mounting a bag system in a centrifuge. In addition, there may be kinking (torsion or sharp bending) of tubing which may affect how the bag system operates during a separation process.

Embodiments of the present invention have been made in light of these and other considerations. However, the relatively specific problems discussed above do not limit the applicability of the embodiments of the present invention.

SUMMARY

The summary is provided to introduce aspects of some embodiments of the present invention in a simplified form, and is not intended to identify key or essential elements of the claimed invention, nor is it intended to limit the scope of the claims.

Embodiments provide for a system box that holds a bag system used with a centrifuge apparatus to separate a composite liquid into components. In some embodiments, the composite liquid may be whole blood. The system box may include a first chamber with a first opening for inserting a first bag of the bag system, a second chamber with a second opening for inserting a second bag of the bag system, and a lid that is moveable from an open position to a closed position where it covers at least a portion of the first chamber. In embodiments, the lid may include an interior surface and an exterior surface. When the lid is closed, the inside surface may cover at least a portion of the first chamber. The inside surface may include a frangible breaking ridge that when the lid is closed is positioned over a recess. When a frangible is placed over the recess, and the lid is closed, the ridge presses down on the frangible and breaks a pin within the frangible. The frangible is then opened without the need for an operator to directly manipulate the frangible. In some embodiments, the lid may also include a tube securing ridge, which may push against tubing to ensure tubing stays positioned in a channel adjacent one or more sensor(s).

In other embodiments, the system box may include one or more tubing guide posts. The tubing guide posts allow different tubing lengths to be wrapped around the guide posts in different ways. Accordingly, bag systems with varying tubing lengths may be used in the system boxes that include the tubing guide posts.

Some embodiments provide for a system box to include a tubing holder for holding segments of tubing. In embodiments, segments of tubing containing whole blood may be placed inside the tubing holder. The tubing holder may be angled with respect to an axis of rotation of a centrifuge apparatus, which may result in centrifugal force maintaining the tubing segments in the tubing holder.

In embodiments, a system box may include a latch system for engaging a lid. In addition, the latch system may be connected to valves so that when a lid is closed and engaged by the latch system, the valves may be closed. When the lid is not engaged with the latch system, the valves may be open. In some embodiments, the valves may remain closed even after the lid is opened, such as for example after a separation process has been completed.

Other embodiments provide for a system box with a liquid guard. The liquid guard may include a curved wall that is designed to catch liquid that may leak from a bag system mounted on the system box. The curved wall may extend above most if not all of the features of the system box to catch liquid and direct it into chambers in the system box. In some embodiments, liquid guard (or other portion of an outer wall) may include some indicia indicating, e.g., such as to an operator, a particular component so that a bag of the bag system that will store the component is placed in a corresponding chamber.

Embodiments also provide for a system for separating components from a composite liquid. The system may include a bag system with a first bag for storing the composite liquid (e.g., whole blood) and a second bag for storing at least one component separated from the composite liquid. The system may further include a system box for holding the bag system during separation. The system box includes a first chamber for storing the first bag and a second chamber for storing the second bag. In embodiments, the system box may further include a third chamber for storing a third bag, which may contain a preservative solution. The system box may also include a lid for covering at least a portion of the first chamber. The lid includes at least a first ridge for breaking a frangible of the bag system.

Other embodiments provide for methods of separating components from a volume of composite liquid. Methods may include loading a bag system onto a system box. The loading may include positioning a first bag of a bag system into a first chamber of the system box. In embodiments, the first bag comprises a volume of composite liquid (e.g., whole blood). A portion of tubing that connects the first bag to a second bag is then routed. A second bag of the bag system may then be positioned into a second chamber of the system box. The method may then include breaking a frangible to open fluid communication between the first bag and the second bag by closing a lid that covers a portion of the first chamber. The composite liquid may then be separated into a plurality of components (e.g., plasma, platelets, red blood cells). The bag system may then be unloaded from the system box. One of the separated components may be stored in the second bag.

BRIEF DESCRIPTION OF THE DRAWINGS

Non-limiting and non-exhaustive embodiments are described with reference to the following figures.

FIG. 18 illustrates parts of a latch system that may be used for engaging a lid of a chamber and closing valves according to an embodiment.

DETAILED DESCRIPTION

Figure 1:
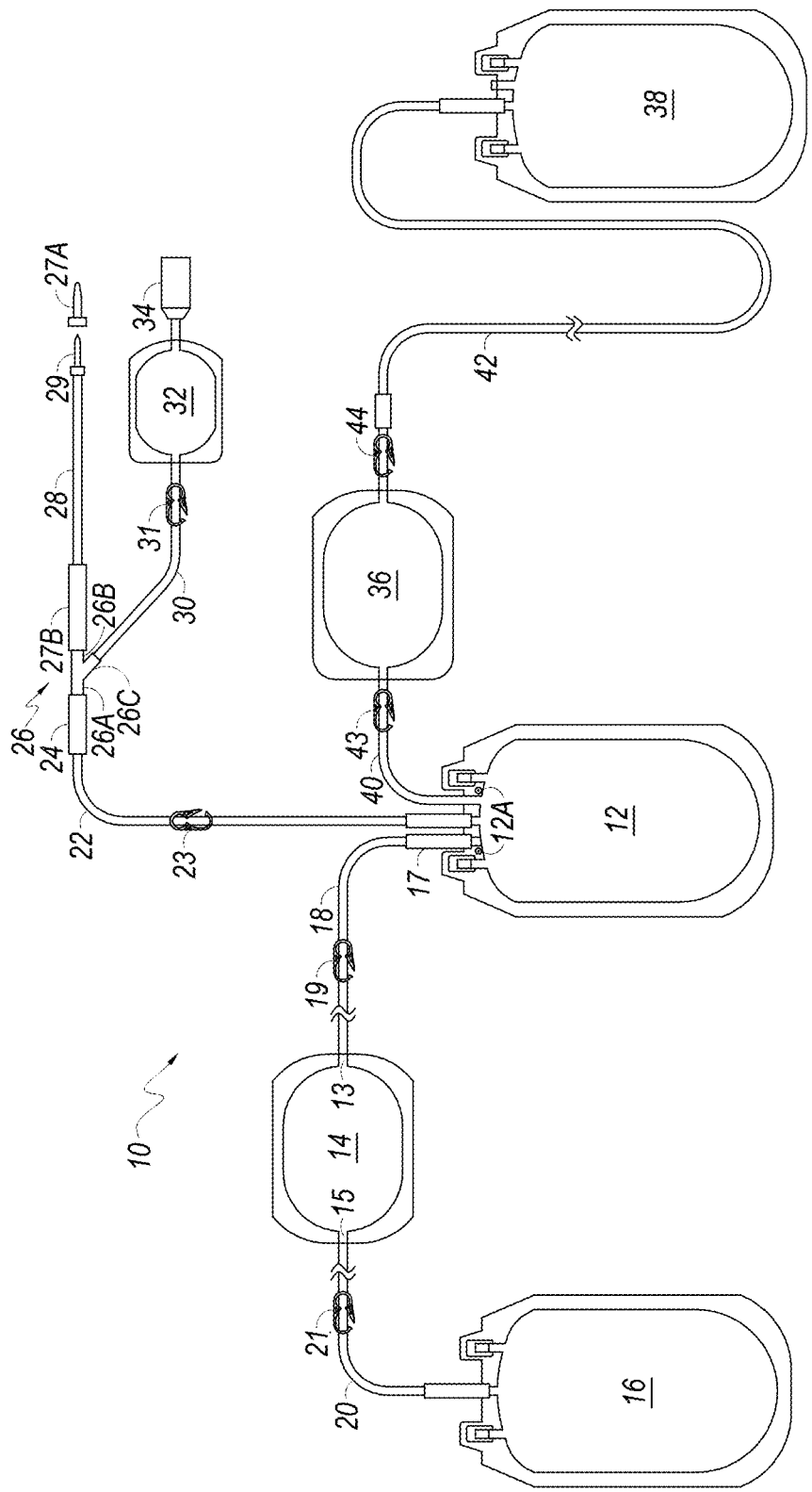
FIG. 1 illustrates a plan view of a bag system according to one embodiment.

The principles of the present invention may be further understood by reference to the following detailed description and the embodiments depicted in the accompanying drawings. It should be understood that although specific features are shown and described below with respect to detailed embodiments, the present invention is not limited to the embodiments described below.

Reference will now be made in detail to the embodiments illustrated in the accompanying drawings and described below. Wherever possible, the same reference numbers are used in the drawings and the description to refer to the same or like parts. Although the description below may be made with respect to the separation of blood, embodiments may be used in separating components from any composite liquid, e.g., biological liquids, organic liquids, or inorganic liquids.

According to embodiments, bag system 10 illustrated in FIG. 1 may be used for separating components from composite liquids, such as by centrifuging. In one embodiment, whole blood containing a plurality of components may be separated into three components, namely a low-density component (relative low-density component), a medium-density component (relative medium-density component) and a high-density component (relative high-density component) (in this embodiment, whole blood is centrifuged into three components including plasma, buffy coat and concentrated red cells), and containing and preserving the components separately in different bags.

As shown in FIG. 1, the bag system 10 may include: a first bag 12 in which, a composite liquid, e.g., blood, containing a plurality of components may be contained; a second bag 14 in which a medium-density component obtained by centrifuging the blood in the first bag 12 may be stored; a third bag 16 in which a low-density component obtained by centrifuging the blood in the first bag 12 may be contained; a first tube 18 through which an upper portion of the first bag 12 and an inlet 13 of the second bag 14 may be connected and through which the low-density component and the medium-density component may be transported from the first bag 12 to the second bag 14; and a second tube 20 by which an outlet 15 of the second bag 14 and the third bag 16 may be connected and through which the low-density component may be transported from the first bag 12 to the third bag 16 by way of the first tube 18 and the second bag 14.

The first bag 12, the second bag 14 and the third bag 16 may each be fabricated by a method in which flexible sheet materials made of a flexible resin such as polyvinyl chloride and/or polyolefin are placed on each other and are fused (by heat fusing or high-frequency fusing) or adhered to each other at peripheral sheet portions into a bag. A first sample bag 32 and a red cell bag 38 may also be in the form of a bag. In other embodiments, 12, 14, 16, 32, and 38 may be in some other form of container.

An anticoagulant may in embodiments be preliminarily contained in the first bag 12. The anticoagulant may be a solution, and non-limiting examples thereof include but are not limited to ACD-A solution, CPD solution, CPDA-1 solution, and heparin sodium solution. The proper amount of anticoagulant corresponding to the amount of blood to be collected may be included in first bag 12.

One end of a blood collection tube (proximal-side blood collection tube) 22 may be connected to an upper portion of the first bag 12. A clamp 23 by which a lumen in the blood collection tube 22 is closed and opened may be provided at an intermediate portion of the blood collection tube 22. One end of a sealing member (e.g., a frangible or clik-tip) 24 may be connected to the other end of the blood collection tube 22. The sealing member 24 may be configured so as to close the channel (which may be provided, at least in part, by a portion of sealing member 24) in an initial condition and to open the channel by a breaking operation.

Such a sealing member 24 as this may include a tube formed, for example, from a flexible resin such as vinyl chloride, and a tubular body which may be connected to the inside of the tube in a liquid-tight manner, may be closed at one end thereof and may have a brittle part at a portion in the longitudinal direction thereof. To put the sealing member 24 into an open (communicating) state, the tubular body may be bent from the outside of the tube by fingers or the like to thereby break the brittle part. Consequently, a channel in the tube which has been closed by the tubular body is opened, whereby the sealing member 24 is put into an open state.

To the other end of the sealing member 24 may be connected a first port 26A of a branch connector 26. To a second port 26B of the branch connector 26, one end of a blood collection tube (distal-side blood collection tube) 28 may be connected, and to the other end of the blood collection tube 28, a blood collection needle 29 may be connected. Before use, a cap 27A may be used to cover the blood collection needle 29, and, after use, a needle guard 27B may be mounted to the blood collection needle 29. The needle guard 27B may be so disposed as to be movable along the longitudinal direction of the blood collection tube 28.

To a third port 26C of the branch connector 26, one end of a branch tube 30 may be connected. At an intermediate portion of the branch tube 30, a clamp 31 may be provided by which a channel in the branch tube 30 may be closed and opened. To the other end of the branch tube 30, bag 32 may be connected. At the time of collecting blood from a donor, a predetermined amount of blood may be first collected in sample bag 32, before collecting the blood in first bag 12. In this case, the sealing member 24 may be kept in a closed state (initial state), the clamp 31 may be in an open state, whereby the blood is inhibited from flowing to the blood collection tube 22 and to the first bag 12. The blood therefore may first flow into the sample bag 32 through the blood collection tube 28, the branch connector 26 and the branch tube 30.

A sampling port 34 may be connected to the sample bag 32, and, by attaching a blood collection tube to the sampling port 34, the collected blood may be sampled into the blood collection tube. The samples of collected blood may be used for testing. Depending on the use, the part(s) ranging from the branch connector 26 to the sampling port 34 may be omitted.

The bag 14 may be used in embodiments to contain (store) buffy coat. Bag 14 may have a bag structure of a top-and-bottom form wherein the inlet 13 is provided at one end and the outlet 15 is provided at the other end. The bag 14 is so set as to have a necessary and sufficient capacity, taking into account the amount of buffy coat to be collected; though the capacity may be smaller than the capacity of the first bag 12. The bag 16 may contain (store) and preserve plasma.

The first tube 18 may be connected to an upper portion of the first bag 12. In embodiments, a sealing member 17 (e.g., frangible, clik-tip, etc.) may be provided at that end portion of the first tube 18 which is located on the first 12 side. The sealing member 17 may have the same, or a similar, configuration and function as sealing member 24, described above. In addition, a first clamp 19 by which a channel in the first tube 18 may be closed and opened may be provided at an intermediate portion of the first tube 18.

The second tube 20 may be connected at its one end to the outlet 15 of the bag 14, and may be connected at its other end to the bag 16. A second clamp 21, by which a channel in the second tube 20 may be closed and opened, may be provided at an intermediate portion of the second tube 20.

As shown in FIG. 1, the bag system according to this embodiment may further include a bag 38 into which concentrated red blood cells may be stored, a filter 36 which may be disposed between the first bag 12 and the red cell bag 38 and by which predetermined cells (e.g., leukocytes) may be removed, a third tube 40 connecting an upper portion of the first bag 12 and an inlet of the filter 36, and a fourth tube 42 through which an outlet of the filter 36 and the red cell bag 38 may be connected. In some embodiment, the filter 36 is configured as a leukocyte removal filter.

In other embodiments, bag 38 may store a preservative solution that may be added to first bag 12 after other components have been removed. In these embodiments, filter 36 may not be a part of system 10.

A clamp 43 by which a channel in the third tube 40 is closed and opened is provided at an intermediate portion of the third tube 40. A clamp 44 by which a channel in the fourth tube 42 is closed and opened is provided at an intermediate portion of the fourth tube 42.

Each of the tubes (inclusive of the first tube 18 and the second tube 20) in the bag system 10 may be made of a transparent flexible resin and a lumen extending between opposite ends of the tube. Each of the clamps (inclusive of the first clamp 19 and the second clamp 21) may be a standard pinch clamp in some embodiments. In addition, in some embodiments, the clamps may have different colors according to the locations of use and their intended use. At the time of sterilization and during stock before use of the bag system 10, each of the clamps may be in an open state and the inside of each of the bags is in communication to uniformly sterilize the system.

Figure 2:
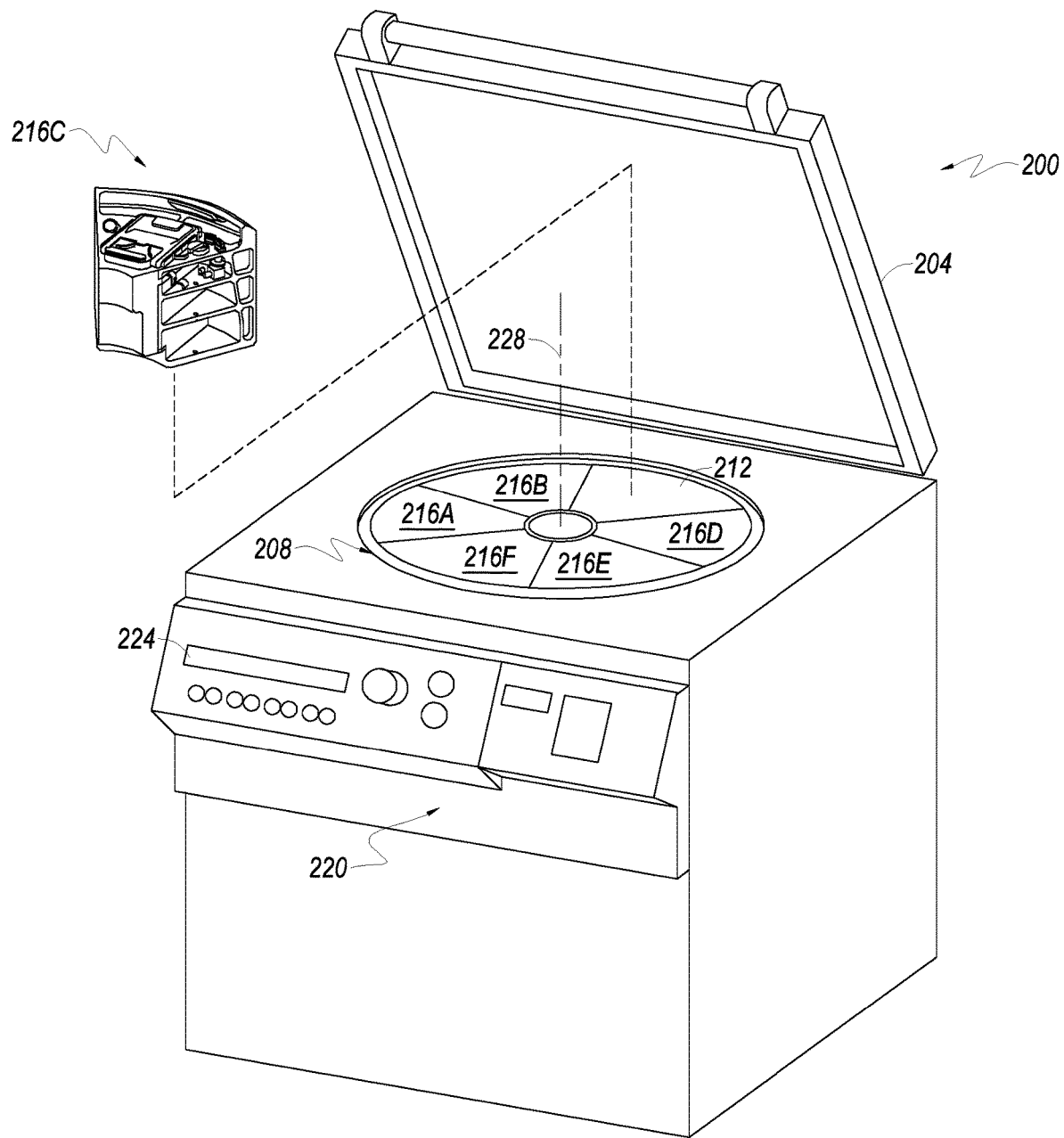
FIG. 2 illustrates a perspective view of a centrifuge apparatus for separating blood according to one embodiment.

The bag system 10 can be used, in embodiments for example, by being mounted to a centrifuge apparatus 200 as shown in FIG. 2. This apparatus 200 may be used for separating whole blood contained in the first bag 12 into three layers (components) including plasma, buffy coat and concentrated red blood cells, storing the buffy coat in bag 14, while storing the plasma in bag 16, and leaving concentrated red blood cells in bag 12. As noted above, bag 38 may include a preservative solution that can then be added to bag 12 to preserve the red blood cells.

It is noted that although FIG. 1 illustrates a specific embodiment of a system with bags and tubing connected in a particular way, other embodiments may provide a system with different connections. For example, in some embodiments, tube 40 and tube 18 may be connected to a branch connector, such as branch connector 26. A tube may connect the branch connector to bag 12, with tube 40 and tube 18 also being connected to the branch connector. As another example, in some embodiments, bag 14 may not be in-line with bag 16 and instead may be connected to a branch connector that is also connected to tube 18. These are merely some examples and the present invention is not limited to any specific connections or arrangement of tubes and bags.

For purposes of illustration, a method for using the bag system 10 (consistent with one embodiment) will be explained. As shown in FIG. 2, the centrifuge apparatus 200 may be box-shaped, and may include an openable/closable cover 204 at the top, a centrifugal drum (means for centrifuging) 208 in the inside, six unit insertion holes 212 provided at regular angular intervals inside the centrifugal drum 208, and six system boxes 216A-F inserted in respective ones of the unit insertion holes. The apparatus 200 may be operated based on UI controls on a console section 220 provided at the front surface, which may be controlled by a microcomputer, and may be configured to display predetermined information on a display 224.

In embodiments, the bag system is loaded onto a system box such as system box 216c. The system box has chambers and features that allow the tubing and bags to be positioned in the system box. Examples of some features of a system box are described below. The system box may be already installed in apparatus 200 before the bag system is loaded onto the system box. In some embodiments, the system box may be out of the apparatus and the system box may be positioned inside a separation apparatus such as centrifuge apparatus 200 after the bag system is loaded.

It is noted that although the system box 216c is shown with a particular shape, in other embodiments (such as the ones described below) the shape may be different and correspond to the shape of unit insertion holes in the separation apparatus.

In the embodiment of FIG. 2, apparatus 200 has six slots where six system boxes may 216A-F be loaded into apparatus 200. In embodiments, system boxes 216A-F are loaded into apparatus 200. Six bag systems, e.g., system 10, may then be loaded into apparatus 200 with one bag system being loaded into each of system boxes 216A-F. Each of the bag systems mounted into system boxes 216A-F may include a bag with a composite liquid, e.g., whole blood. Apparatus 200 creates a centrifugal field by spinning centrifugal drum 208 and system boxes 216A-F around the axis of rotation 228. The centrifugal field then separates the composite liquid loaded onto system boxes 216A-F into components, e.g., whole blood into, plasma, buffy coat, and red blood cells. As may be appreciated, the strength of the centrifugal field in apparatus 200 increases as you move away from the axis of rotation 228.

Figure 3:
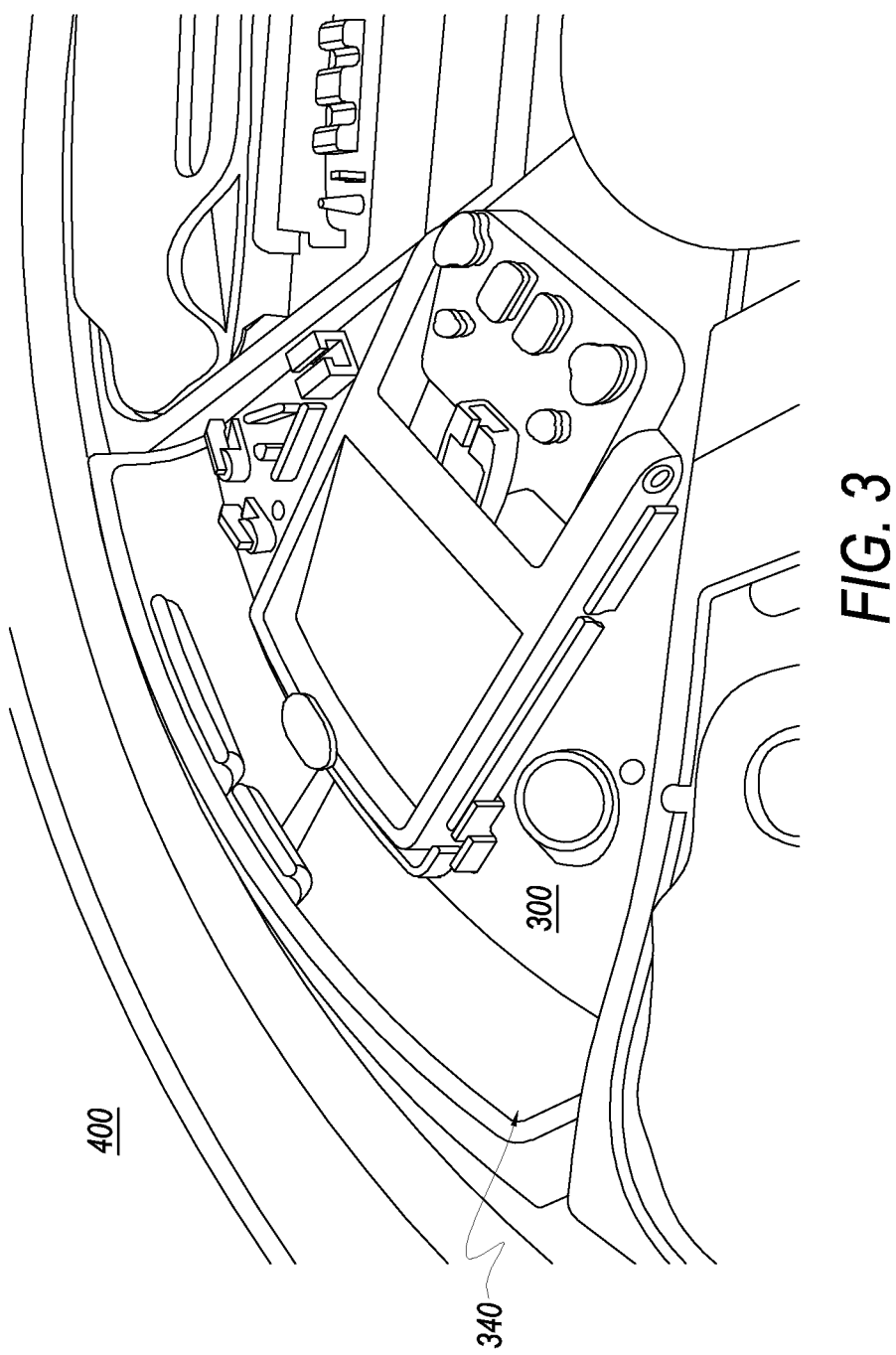
FIG. 3 illustrates a system box installed in a centrifuge apparatus according to an embodiment.
Figure 4:
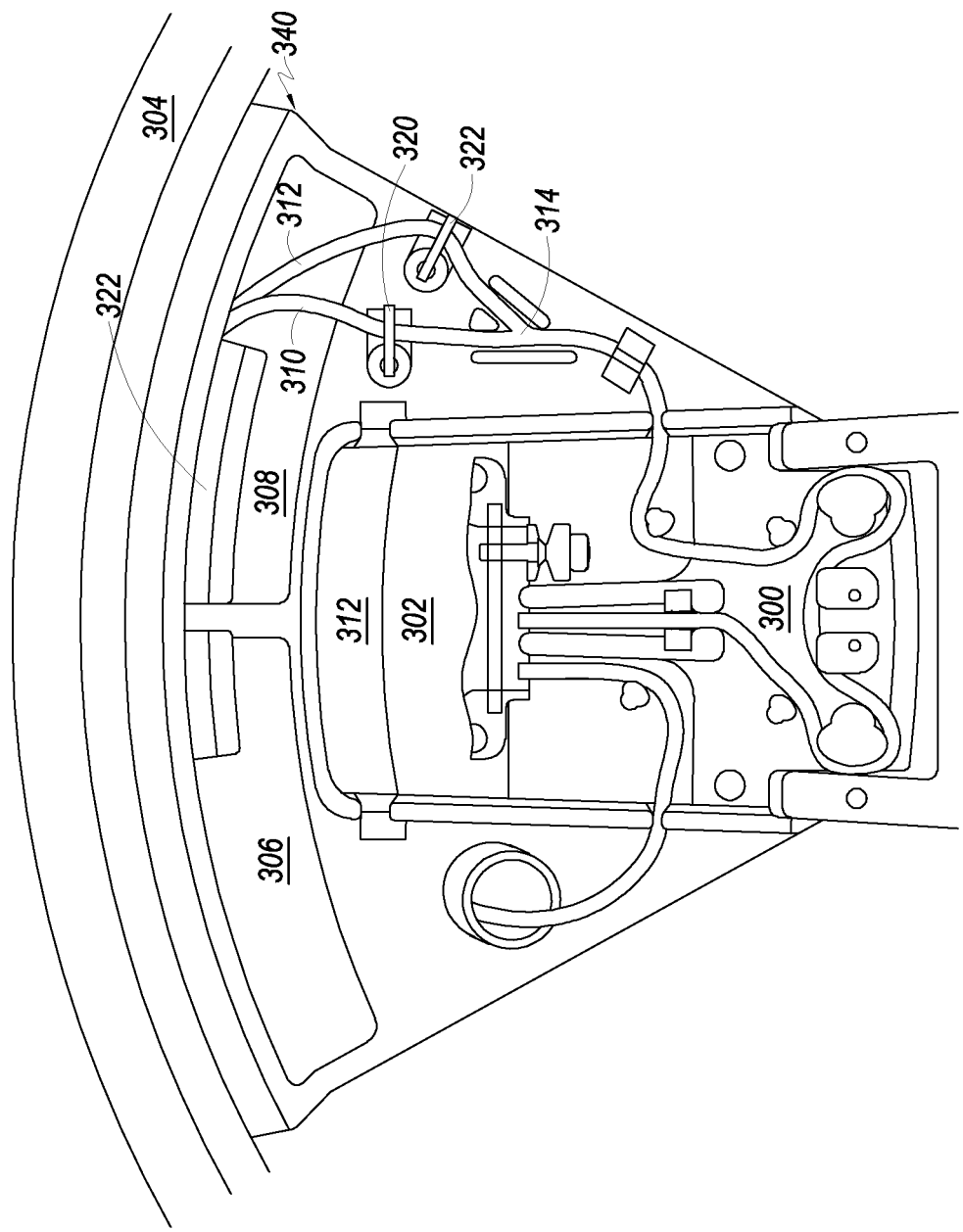
FIG. 4 illustrates another view of a system box installed in a centrifuge apparatus with a bag system positioned in a chamber of the system box according to an embodiment.

FIGS. 3 and 4 illustrate a system box 300 installed in a centrifuge apparatus 400 according to an embodiment. FIGS. 5-10 illustrate system box 300 standing alone (e.g., not installed in a centrifuge apparatus) according to an embodiment.

In FIG. 4 a bag 302 is positioned in a chamber 304 of the system box 300. Chamber 304 has an opening 305 for positioning bag 302 in chamber 304. The bag 302 may be part of a bag system such as system 10 described above with respect to FIG. 1. In some embodiments, bag 302 may be bag 12 and contain a composite liquid such as whole blood for separation into components. In these embodiments, bags in chambers 306 and 308 may correspond to one or more bags 14, 16, and/or 38 shown in FIG. 1 and described above. Also, tubes 310 and 312 may in embodiments correspond to tubes 18 and 40, except that they may be connected to a branch connector 314 in the embodiment shown in FIG. 4. As described in greater detail below, system box 300 include features that allow a bag system (e.g., system 10) to be easily mounted making a process of separating a composite liquid, such as whole blood, more efficient.

Figure 5:
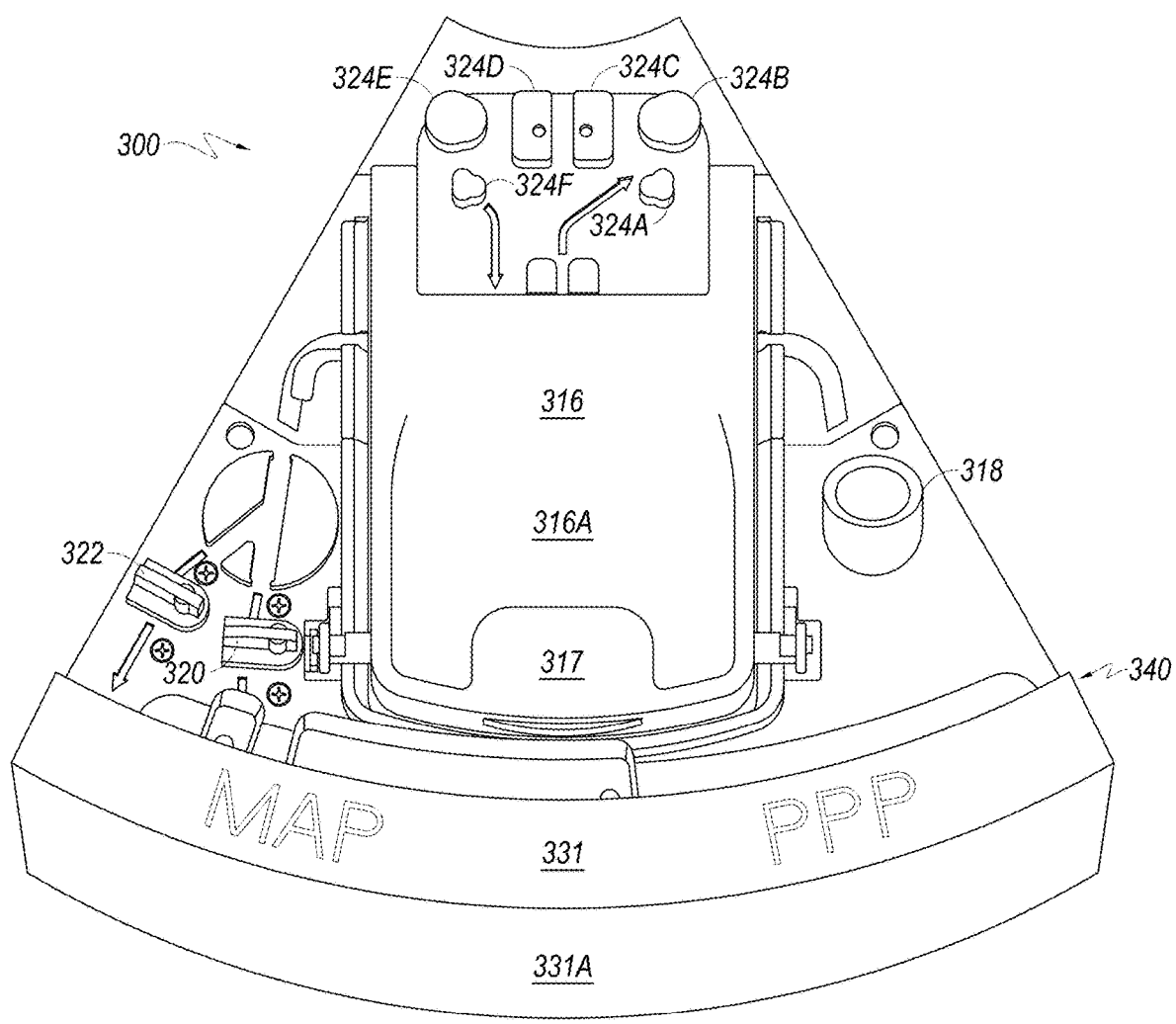
FIG. 5 illustrates a system box standing alone (e.g., not installed in a centrifuge apparatus) according to an embodiment.
Figure 6:
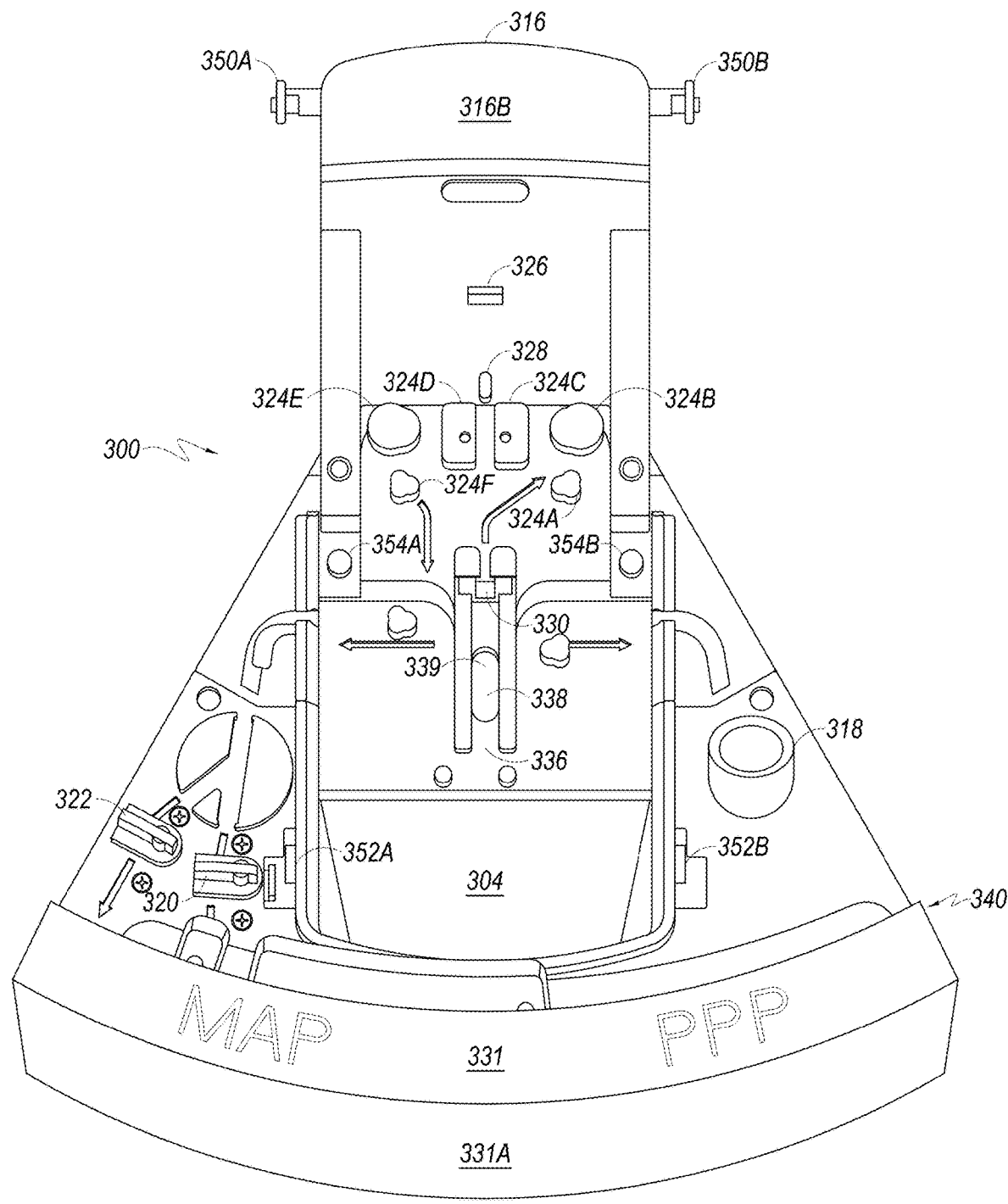
FIG. 6 illustrates the system box of FIG. 5 with a lid in an open position to show a chamber according to an embodiment.
Figure 7:
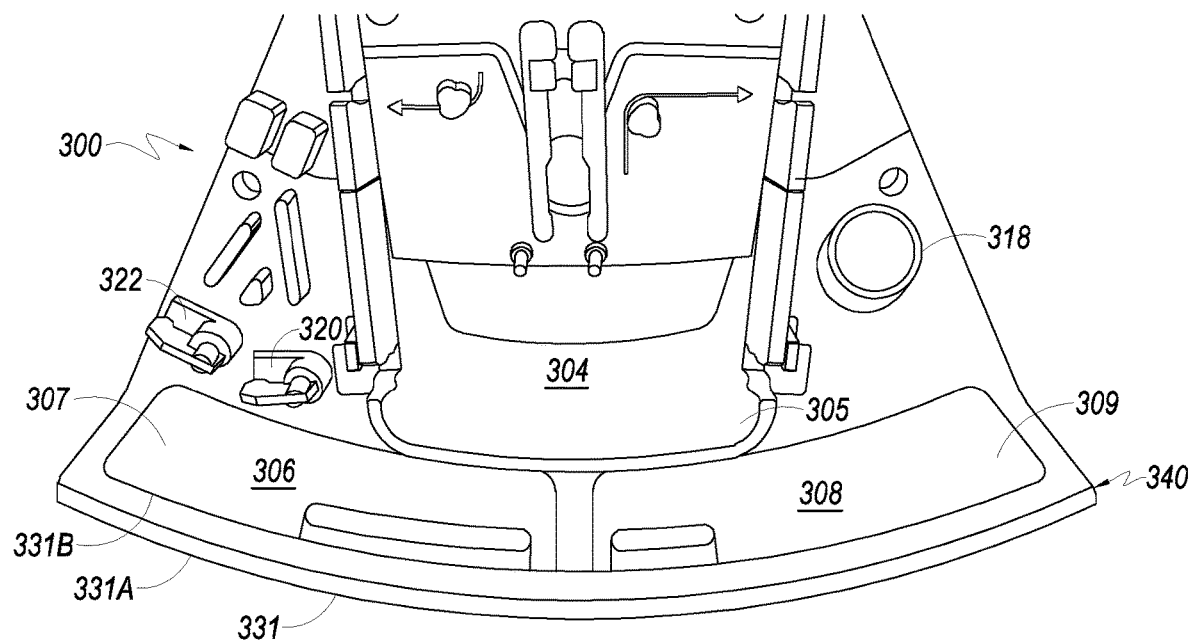
FIG. 7 illustrates a closer view of the chamber of the system box shown in FIG. 6.

As shown in FIGS. 5-10, system box 300 includes a chamber 304 (FIG. 6) for positioning a bag of a composite liquid (e.g., whole blood) and chambers 306 and 308 (FIG. 7). In addition, chamber 304 includes a lid 316 that covers chamber 304. Lid 316 includes an exterior surface 316A (FIG. 5) and interior surface 316B (FIG. 6). A handle 317 on the exterior surface 316A allows an operator to move lid 316 from an open position to a closed position.

Further, system box 300 includes tubing holder 318 (FIGS. 5-9), valves 322 and 320 (FIGS. 5-8), a number of guide posts 324A-F, a clik-tip or frangible breaking feature, e.g., ridge 326 on interior surface 316B, a liquid guard 340 on a top portion of outer wall 331, and a tube securing ridge 328 on interior surface 316B. Additionally, lid 316 also includes a first arm 350A and a second arm 350B, which as described below may engage with hooks of a latch system when lid 316 is closed.

FIGS. 5-10 illustrates that system box 300 generally has a wedge shape with an outer wall 331. The wedge shape corresponds to the shape of a space in a separation apparatus, e.g., apparatus 200 or 400 where the system box 300 is placed for separating components from a composite liquid. It is noted that in other embodiments, system box 300 may have other general shapes (e.g., cube, cylinder, prism, etc.) that correspond to a space in a separation apparatus. Outer wall 331 of system box includes a curved outer surface 331A and an inner surface 331B. However, it is noted that in other embodiments, outer wall 331 and surfaces 331A and 331B may have straight features, curved features, projections, perforations, or a combination of features.

FIG. 5 shows system box 300 with lid 316 closed. In embodiments, lid 316 is hinged so that it may be moved from an open position (FIG. 6) to a closed position. FIG. 6 shows system box 300 with the lid 316 in the open position to show the chamber 304, where a container, e.g., bag, storing a composite liquid, e.g., whole blood, may be positioned for separation. As noted above, the bag may be part of a blood bag system. Also shown in FIG. 6, is a sensor 330. At least a portion of tubing that is part of a bag system is positioned in sensor 330 to detect the presence of the various components, after separation, as they are being transferred to bags for storage.

FIG. 7 shows a close up view of system box 300. In addition to chamber 304, chambers 306 and 308 are shown. In embodiments, chambers 306 and 308 may hold bags that are used to store components of whole blood after separation, or bags with additive solution which is used for adding to separated components.

As shown in FIG. 7, chamber 306 includes an opening 307 through which a bag from a bag system in positioned in chamber 306. Chamber 308 may be adjacent to chamber 307 and includes an opening 309 through which a bag from a bag system in positioned in chamber 308.

Chambers 306 and 308 may be located such that when system box 300 is placed in a centrifugal separation apparatus, chambers 306 and 308 may be positioned further away from a central axis of rotation, with chamber 304 being closer to the axis of rotation. System box 300, including bags loaded onto system box 300, may then be subjected to a centrifugal field which separates the composite liquid into components.

Chamber 306 and chamber 308 may be, at least partially, between chamber 302 and outer wall 331. With this arrangement of the chambers, chambers 306 and 308 will be in a higher force region (compared to chamber 304) closer to outer wall 331 when subjected to a centrifugal field. The axis of rotation may be located on the side of system box 300 closer to guide posts 324D and 324C (FIG. 5). Being in a higher force region may allow components to flow, after separation, from a bag in chamber 302 to one or more bags in chambers 306 and/or 308. As described in greater detail below, in some embodiments, there may be a tubing path located between chamber 306 (and/or 308) and outer wall 331. Having a tubing path that is in a higher force region than a bag in chamber 306 (and/or 308) may provide some advantages as described below.

In some embodiments, the size and shape of chambers 306 and 308 may be different, while in others they may be generally the same. Making chamber 306 and 308 different shapes or sizes may provide some benefits. For example, a provider may be confused as to which specific bag (e.g., an empty bag for storing a component such as plasma or a bag full of preservative) of a bag system should be placed in a chamber. The shape and/or size of a chamber may be such that only the specific bag that should be in the chamber can easily fit in the chamber. If an operator attempts to place a different bag in the chamber, it may be more difficult, which may indicate to the operator that the operator is attempting to place a bag in a chamber that is designed for a different bag.

Figure 8:
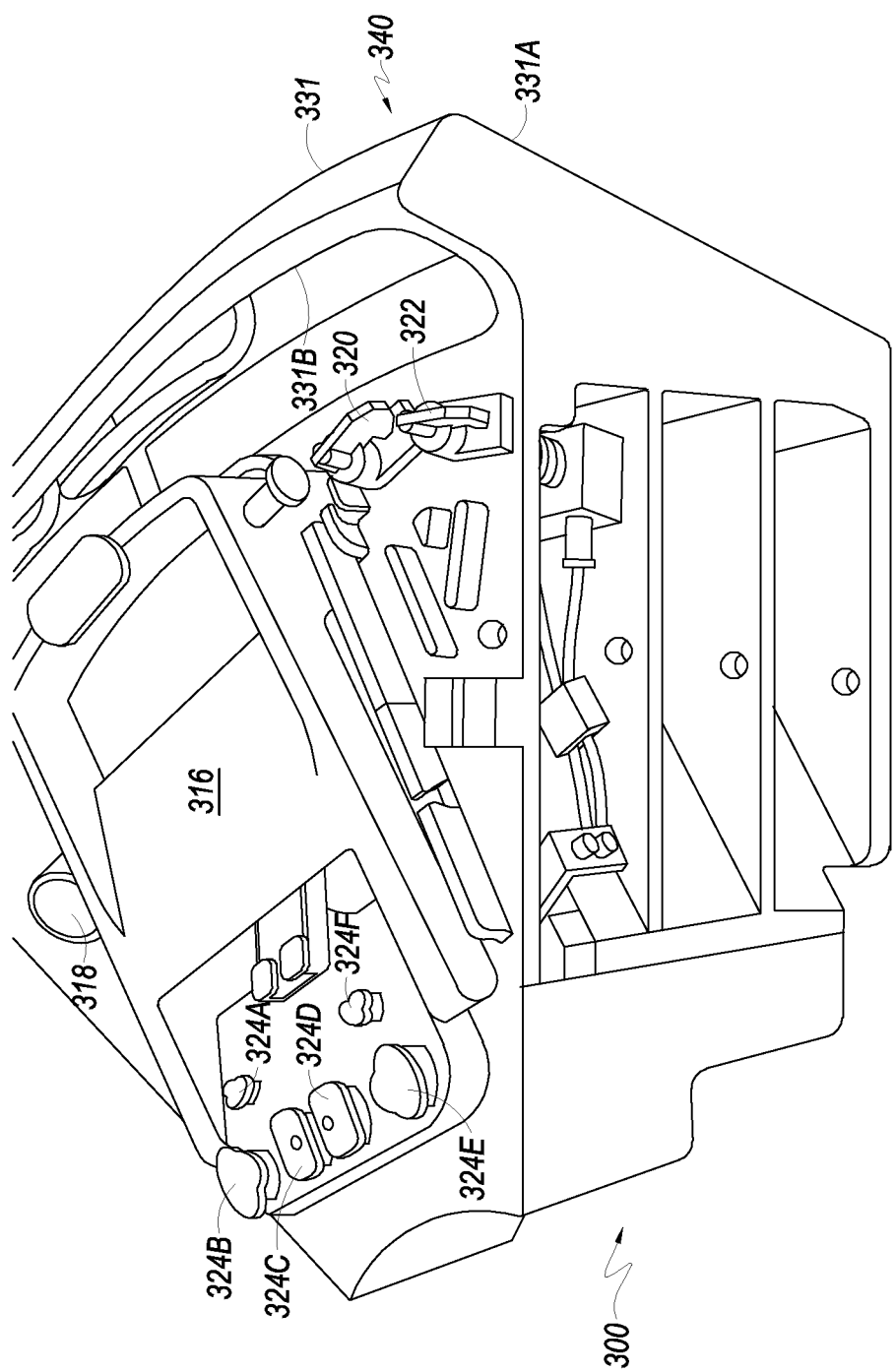
FIG. 8 illustrates a side perspective view of the system box shown in FIGS. 3-7.
Figure 9:
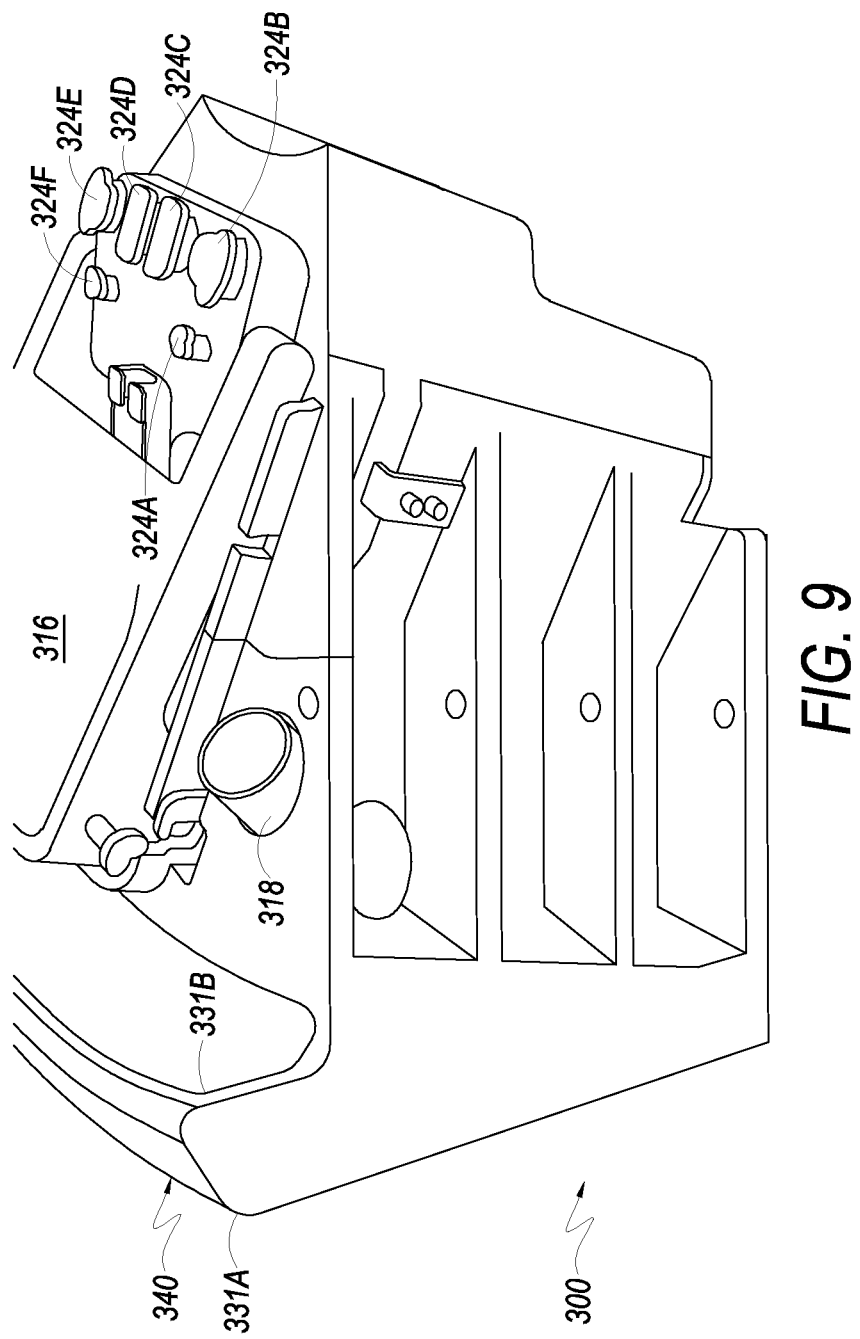
FIG. 9 illustrates a different side view of the chamber of the system box shown in FIGS. 3-8.
Figure 10:
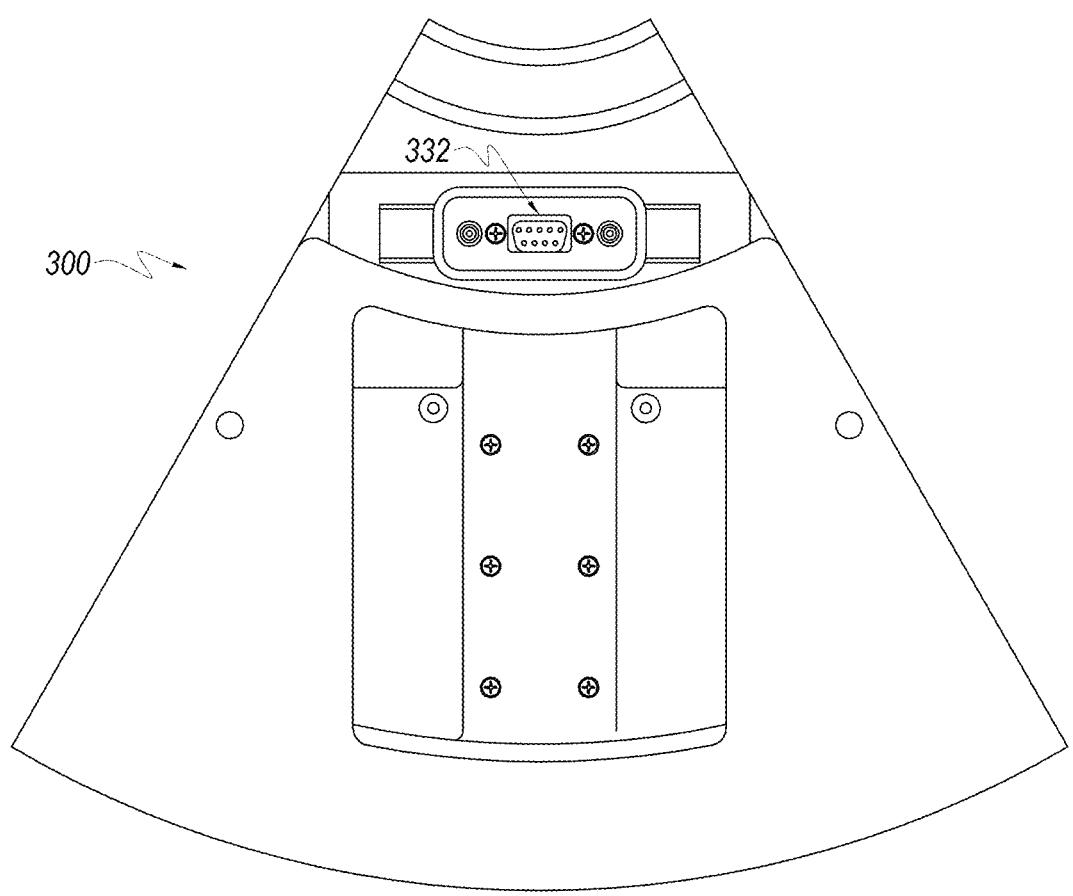
FIG. 10 illustrates a bottom view of system box shown in FIGS. 3-9.

FIGS. 8 and 9 show different sides of the system box 300 including several of the features, which are described in greater detail below. FIG. 10 shows a bottom view of the system box 300. FIG. 10 shows a connector 332, which may be used to connect to electronic components (e.g., a microprocessor, user interface controls, a monitor, memory, etc.) that may be part of a centrifuge apparatus, e.g., apparatus 200 or apparatus 400.

As described above, system box 300 may include a tubing holder (e.g., tubing holder 318). In some processing of whole blood, a length of tubing that holds some whole blood may be segmented into portions. The segmenting may be performed by an operator using a sealer that seals (e.g., by welding the tubing) whole blood in small segments along the length of tubing. As whole blood in a blood bag, e.g., bag 302, is centrifuged and separated into components, the whole blood in the individual segments is also separated. After the processing, an operator can then look at the segments to gauge how well the separation of the whole blood has proceeded. Also, the segments provide samples that can be used to determine qualities of the blood being separated, e.g., hematocrit. In conventional systems, the tubing segments are stuffed in a separation chamber or in chambers with other bags of a bag system.

Figure 11:
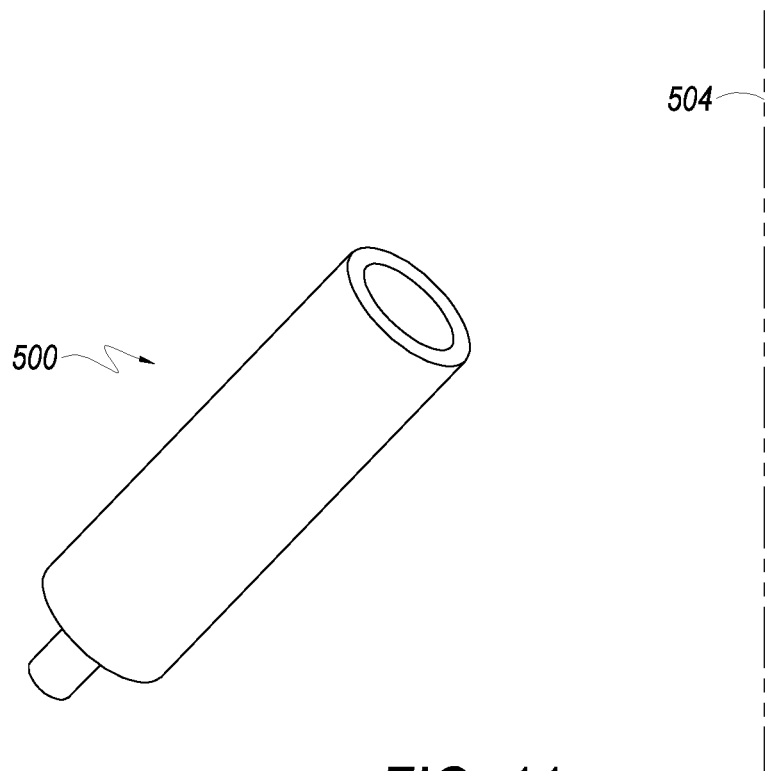
FIG. 11 illustrates a tubing holder that may be used in embodiments.

According to embodiments of the present invention, the segmented portions of tubing may be stored in a tubing holder (e.g., tubing holder 318) designed specifically for holding segments of tubing with whole blood. FIG. 11 illustrates a holder 500 that may be included in embodiments as tubing holder 318 (FIGS. 3-10). As shown in FIG. 11, tubing holder 500 is angled, with respect to an axis of rotation 504 (e.g., axis 228, FIG. 2) such that when a centrifuge apparatus is in operation, centrifugal force will keep the tube segments in the tubing holder.

Figure 12:
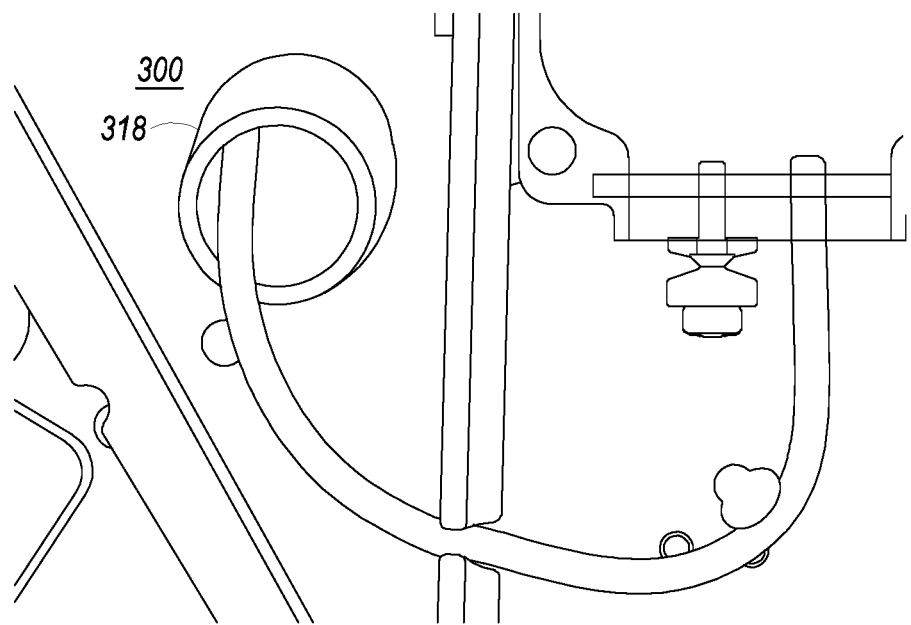
FIG. 12 illustrates a closer view of a system box in a centrifuge apparatus with a tubing holder according to an embodiment.

FIG. 12 shows a close-up view of tubing holder 318 in box 300. In FIG. 12, tubing holder 318 is holding tubing segments. One feature of tube holder 318 is the ability to easily remove and replace tubing holder 318. In situations where a tubing segment bursts and whole blood leaks in tubing holder 318, the tubing holder 318 may be easily removed to be cleaned and/or replaced.

Figure 13:
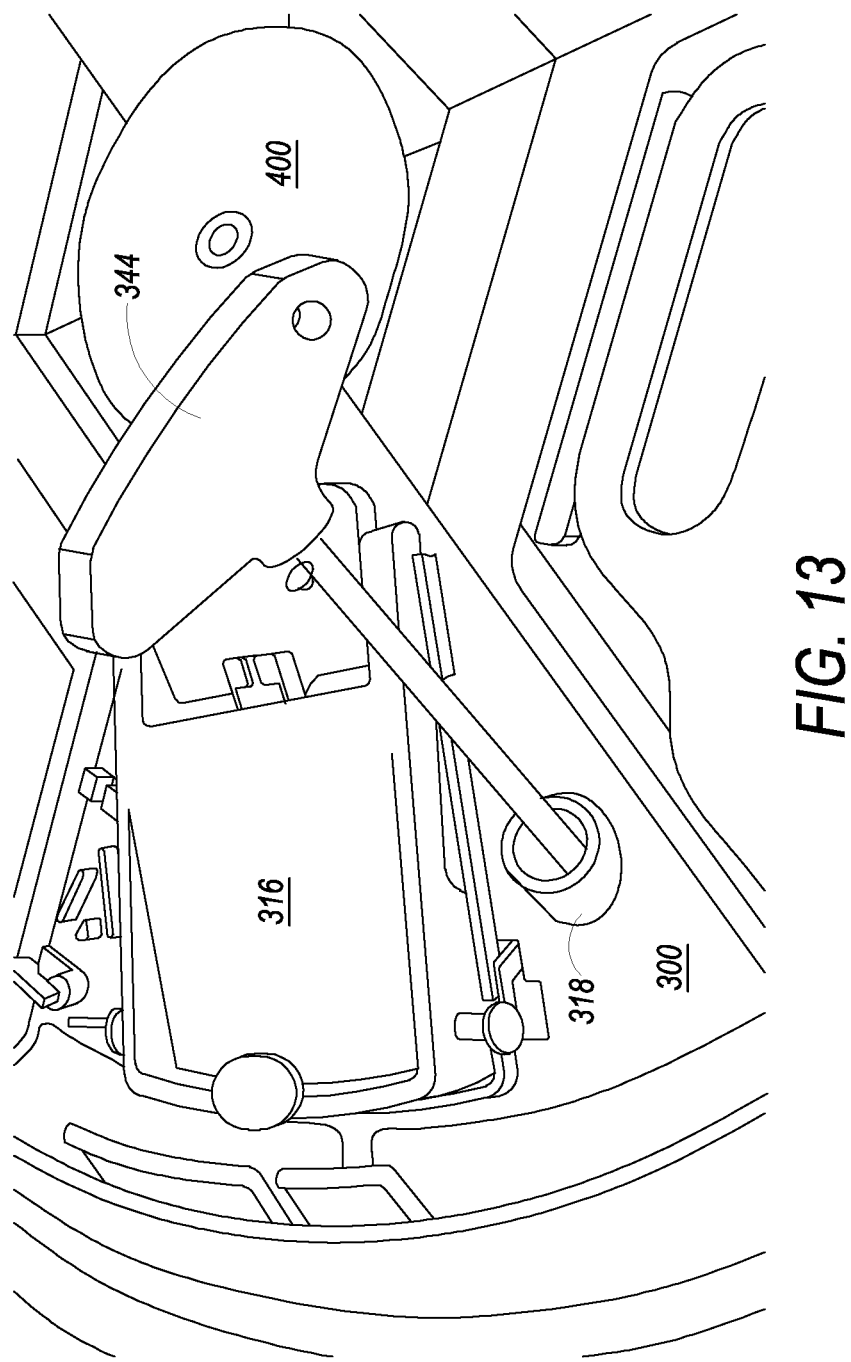
FIG. 13 illustrates a view of the system box of FIGS. 3-10 in a centrifuge apparatus with a tubing holder being installed (in)/removed (from) the system box.

FIG. 13 shows a tool 334 that may be used to loosen or tighten a fastener (not shown) that attaches tubing holder 318 to system box 300. A fastener, e.g., a screw, bolt, etc., may be positioned inside holder 318 that in some embodiments may be located at a bottom end of holder 318. Tubing holder 318 may include a hole at the bottom end that allows a screw to attach holder 318 to system box 300.

Figure 14:
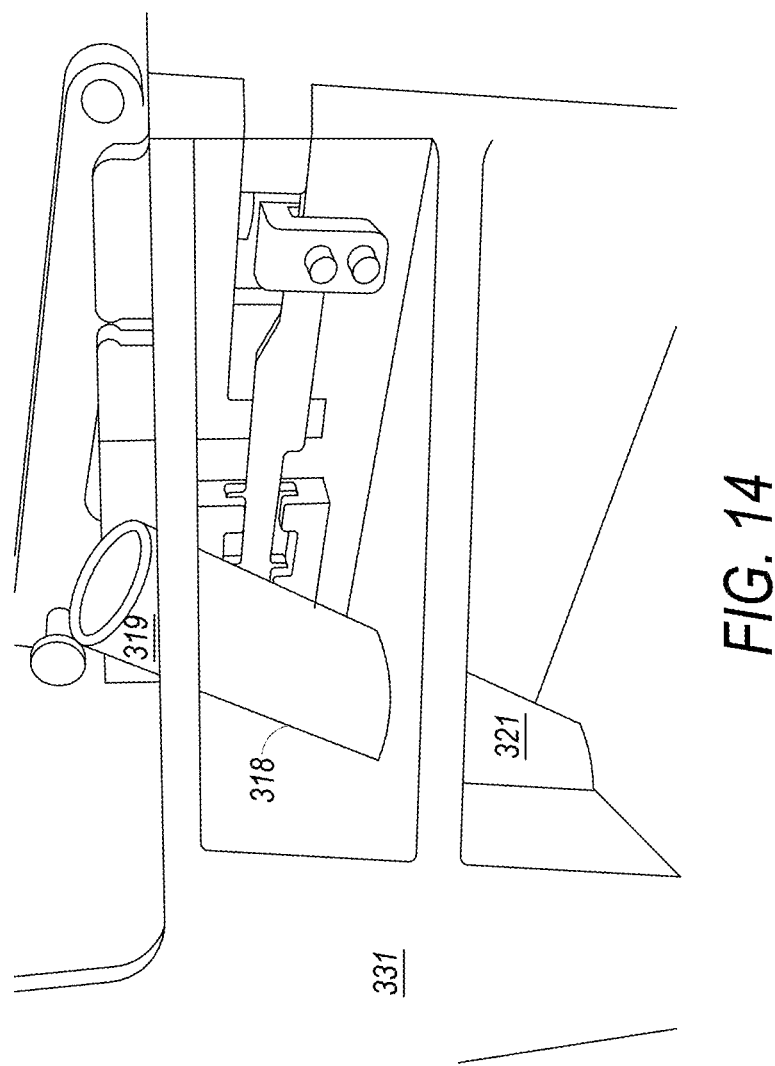
FIG. 14 illustrates a side view of the tubing holder as installed in the system box according to an embodiment.

FIG. 14 illustrates tubing holder 318, which as noted above is oriented at an angle consistent with some embodiments. In these embodiments, when system box 300 is placed in a centrifuge apparatus, holder 318 will be oriented at an angle. In the embodiment shown in FIG. 14, the distal end 321 of holder 318 may be closer to outer wall 331 while the proximal end 319 may be further away from outer wall 331. In embodiments, this orientation will maintain the tubing segments in holder 318 using the centrifugal force generated from spinning of the centrifuge apparatus.

In addition to tubing holders, embodiments may also provide for a lid that encloses the chamber where the whole blood bag is positioned. The lid may include additional features. Referring back to FIG. 6, lid 316 of system box 300 is shown opened. Lid 316 includes hinges that allow it to be hinged open and closed. Lid 316 allows the whole blood bag positioned in chamber 304 respectively, to be fully contained from all sides. This may be helpful so that a bag positioned in the chamber is not extended (e.g., expands), during centrifugation, causing some other location to collapse, making removal of all of the components from the bag after separation more difficult.

Additionally, embodiments provide a mechanism for automatically opening a sealing member, e.g., a clik-tip or frangible. As described above, some bag systems may include sealing members that seal off bags until the sealing member, e.g., frangible or clik-tip, is opened.

Conventionally, a frangible or clik-tip (e.g., 24 and 27 in FIG. 1) may be opened manually by an operator. An operator may bend a frangible or clik-tip to break an inside pin of the frangible or clik-tip creating fluid communication between two bags. An operator may utilize a relatively large number of bag systems in a day, which may result in wrist strain, hand strain, or a repetitive motion injury from having to manipulate numerous frangibles.

Figure 15:
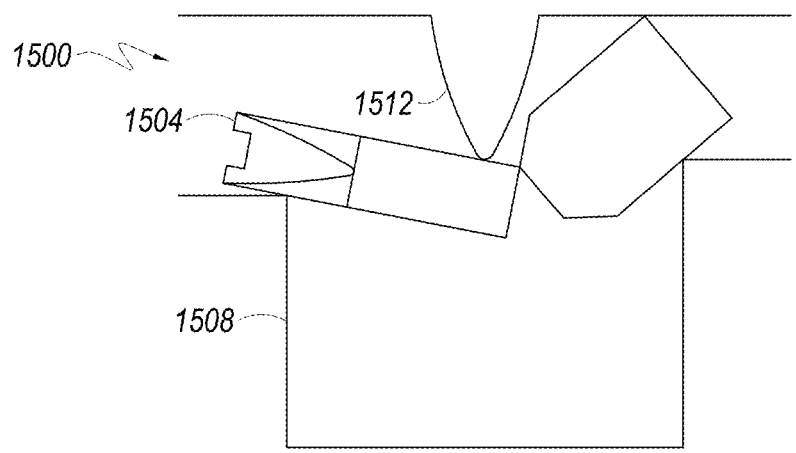
FIG. 15 illustrates an example of a mechanism that may be used to break a frangible according to an embodiment.

Embodiments provide a clik-tip or frangible breaker which may avoid the need for an operator to directly open the frangible or clik-tip. FIG. 15 illustrates an example of a mechanism that may be used to break a frangible or clik-tip according to an embodiment. As illustrated in FIG. 15, a frangible 1504 is positioned over a recess 1508. A ridge 1512, positioned above the recess 1508 and generally located in the middle of the recess 1508, is moved down, which causes the frangible 1504 to break.

Referring back to FIG. 6, system box 300 includes a ridge 326, which may be used as a clik-tip or frangible breaker. As can be appreciated in FIG. 6, ridge 326 is on the interior surface 316B of lid 316. When a bag system is positioned on system box 300, tubing with a frangible may be positioned in a channel 336. An opening 339 of a recess 338 is in channel 336. A frangible may be positioned across opening 339 of recess 338 and when lid 316 is closed, ridge 326 may be pressed down on the frangible which may bend into opening 339, causing a pin in the frangible to break, allowing fluid communication from the bag positioned in chamber 304 to bags positioned in chambers 306 and/or 308.

Another feature of system box 300 is a tube securing ridge 328. Referring to FIG. 6, interior surface 316B of lid 316 includes tube securing ridge 328. In embodiments, when a bag system is positioned in system box 300, a portion of tubing is positioned in channel 336, so that at least a portion of the tubing is positioned adjacent sensor 330. Sensor 330 in embodiments senses components as they flow through the tubing past sensor 330. For example, after separation, plasma may be transferred through the tubing. Sensor 330 may determine when platelets or leucocytes begin to flow in the tube, at which point, valves may be closed/opened depending on the component passing through the sensor. As can be appreciated in FIG. 6, when lid 316 is closed, tube securing ridge 328 presses on the tube in channel 336 to ensure that a portion of the tube stays positioned in channel 336 adjacent sensor 330.

In some embodiments, system box 300 may include a liquid guard, such as liquid guard 340 shown in FIGS. 3-9. Liquid guard 340 forms a top portion of outer wall 331. As may be appreciated, on occasion a bag system mounted on a system box may fail and/or leak causing liquid, e.g., blood or blood components, to leak. If the leak occurs in a centrifuge apparatus during centrifugation, liquid may be spread across the entire centrifuge apparatus requiring significant time to clean and sterilize. Liquid guard 340 may be designed to catch liquid and direct the liquid into one of chambers 306 and/or 308 making clean-up of leaks/spills easier and preventing liquid from spreading across the entire apparatus.

Liquid guard 340 may in embodiments curve toward the first chamber 304, which allows it to catch liquid and direct the liquid into chambers 306 and/or 304. The curved portion extends at least slightly, and in some embodiments significantly, above the other features of the system box, e.g., lid 316 when lid 316 is closed. During centrifugation, liquid that leaks may be directed by centrifugal force toward liquid guard 340. The liquid may then be caught by the curved portion of guard 340 and directed into a chamber(s), e.g., chambers 306 and 308, preventing the liquid from splattering across the entire centrifuge apparatus. The system box may then be removed and any liquid in the chambers cleaned.

As shown in FIG. 6, in some embodiments, a liquid guard, such as guard 316 may include other features. As one example, liquid guard 316 may include indicia indicating the type of bags that may be placed in a chamber, e.g., chambers 308 and 306. As shown in FIG. 6, an outside surface of guard 340 includes the indicia "PPP" and "MAP," indicating a particular component, such as platelet poor plasma "PPP" or a solution to be added to a component after separation, such as mannitol-adenine-phosphate "MAP." These indicia may be helpful to an operator that is loading a bag system in system box 300. The operator may use the indicia to determine the appropriate bag of the bag system to position in each chamber.

Figure 16:
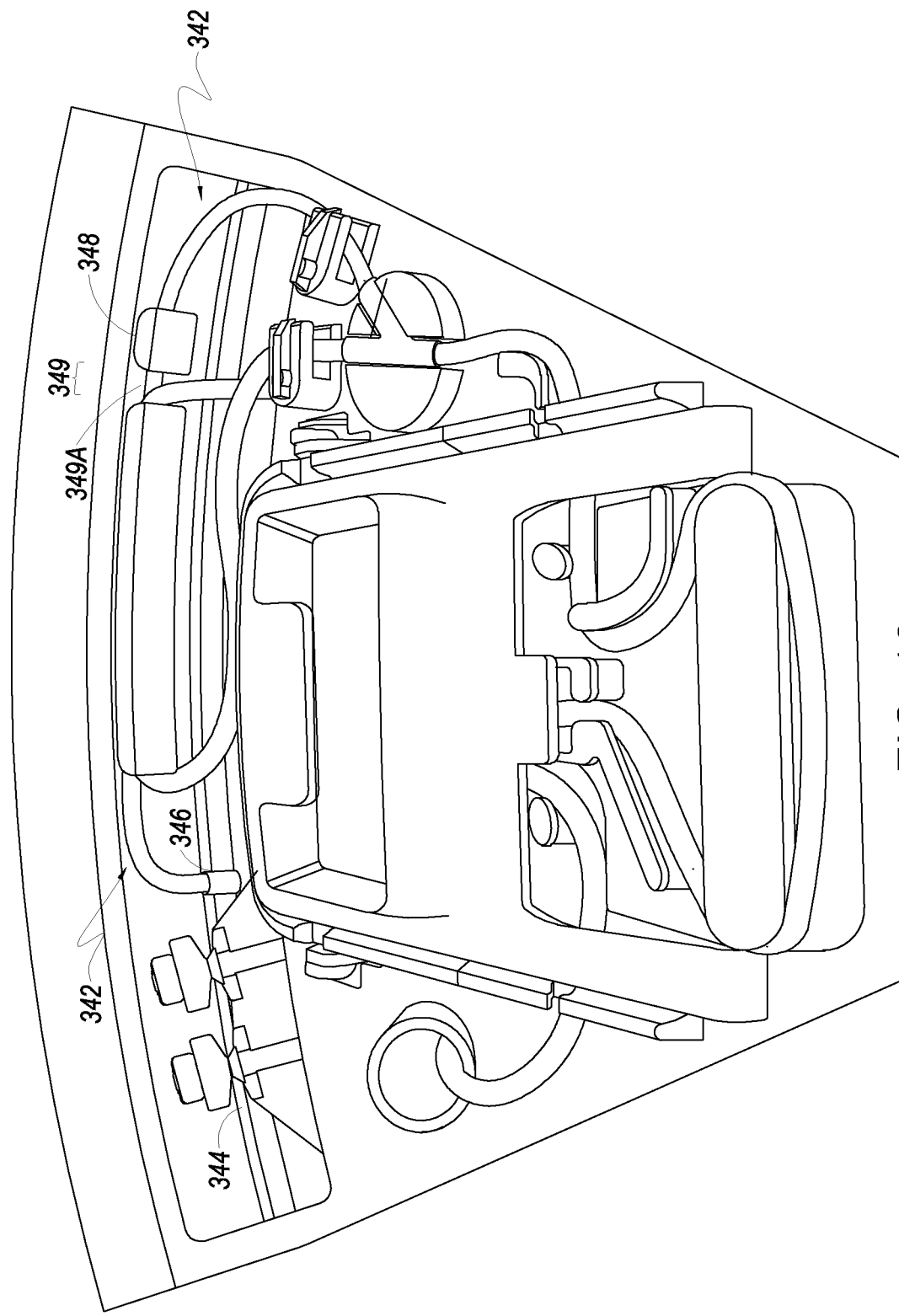
FIG. 16 illustrates an inside surface of an outer wall of the system box showing a tubing path for routing tubing.

In some embodiments, a system box may be designed to ensure that most, if not all, air is pushed out of a component bag and also out of some of the length of tubing connected to the component bag. For example, referring to FIG. 16, it may be desirable to have a component bag, such as a plasma bag, without air and in addition, also a length of tubing, e.g., from the component bag to one of valves 320 and 322, without air. In these embodiments, system box 300 may have a tubing path for routing tubing that connects a first bag of a bag system (e.g., bag 12) with a second bag of the bag system (e.g., bag 16). As shown in FIG. 16, at least a portion of a tubing path 342 may be positioned between the outer wall 331 and the first chamber 304. Indeed, portion 342 is between chambers 306 and 308 and outer wall 331.

As shown in FIG. 16, the chambers 306 and 308 may be positioned closer to an axis of rotation of a centrifuge when the box 300 is in a centrifuge apparatus. This may ensure that an inlet of a bag in one of chambers 306 and 308 is subjected to a lower centrifugal force, than tubing in tubing path portion 342, which may push the air out of the bag and also out of a portion of tubing. In the embodiment shown in FIG. 16, bag inlet 346 is positioned closer to the axis of rotation than the tubing in the tubing path portion 342.

In embodiments, the portion 342 of the tubing path may be provided by a number of features. In the embodiment shown in FIG. 16, a ledge 344 provides the tubing path portion 342. In other embodiments, the tubing path portion 342 may be provided by a channel, hooks, guide posts, ridge, etc. Indeed, as shown in FIG. 16, guide hook 348 is part of tubing path 342 and helps maintain tubing between the outer wall 331 and chambers 306 and 308. Guide hook 348 and the portion of tubing path 342 may also prevent the tubing from kinking.

In some embodiments, the features may provide multiple functions. For example, in some embodiments, guide hook 348 may provide part of a frangible opener 349. A frangible may be positioned in slot 349A of opener 349 and then manipulated by an operator to break the frangible and open communication with a bag of a bag system. In one embodiment, the opener 349 may be provided to open communication to a preservative solution of a bag system, such as a bag filled with MAP. Further, liquid guard 340 may include indicia indicating to an operator the existence of frangible opener 349.

Figure 17A:
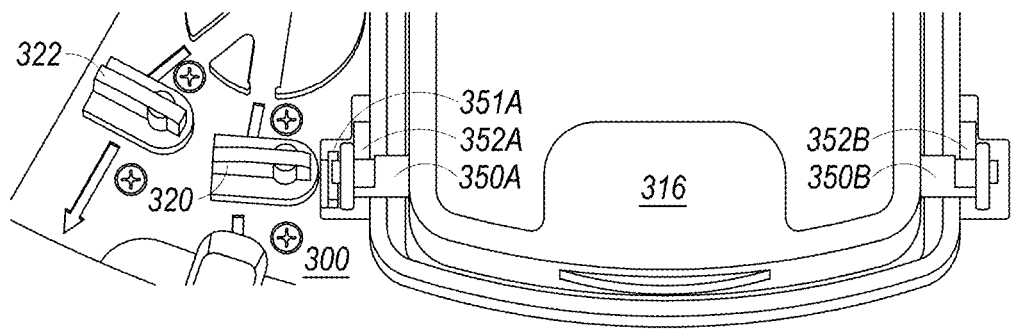
FIGS. 17A and 17B illustrate portions of a latch system that may be used for engaging a lid when in a closed position according to an embodiment.
Figure 17B:
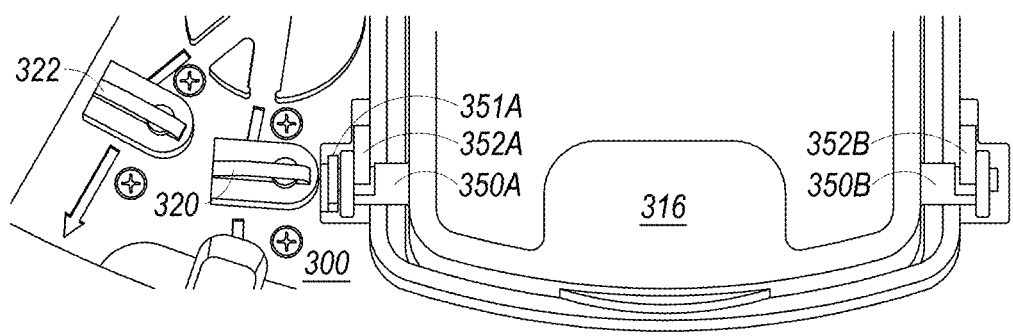

FIGS. 17A and 17B illustrate a latch system for securing a lid of a system box, according to some embodiments. FIGS. 17A and 17B illustrate system box 300 showing lid 316 and valves 320 and 322. Lid 316 comprises two arms 350A and 350B that engage with two hooks 352A and 352B respectively. As shown in FIGS. 17A and 17B, hook 352A engages arm 350A when lid 316 is closed, and hook 352B engages arm 350B when lid 316 is closed. In embodiments, the hooks 352A and 352B may be part of a latch system that secures the lid 316 during processing, and opens the lid after processing.

In one embodiment, the latch system may be connected to valves 320 and 322. In these embodiments, the latch system may work with valves 320 and 322 to ensure that the valves are in an open position whenever lid 316 is not engaged by hooks 352A and/or 352B, as is shown in FIG. 17A. When lid 316 is closed, and hooks 352A and/or 352B engage arms 350A and 350B, the latch system may close valves 320 and 322, as is shown in FIG. 17B.

The latch system may in embodiments include a number of features. For example, in embodiments, the latch system may include hooks, clamps, rods, arms, linkages, sensors, motors, actuators, fasteners, and the like. For example, as shown in FIG. 6, system box 300 may include pushing rods 354A and 354B that push up against lid 316 when a separation process is over. Accordingly, when a separation procedure is over, the hooks 352A and 352B may disengage the arms 350A and 350B of lid 316 and pushing rods 354A and 354B, which in embodiments may be spring loaded, may push up against lid 316 so that lid 316 is unlatched (see e.g., FIG. 13).

FIG. 18 illustrates some features of an embodiment of a latch system 500. Latch system 500 is part of system box 300 (FIGS. 3-10). As shown in FIG. 18, latch system 500 includes linkage arm 502, which is attached to bracket 504 by two fasteners 506A and 506B. Linkage arm 502 may be attached to hooks that engage with arms of lid 316, e.g., arm 350B and arm 350A. In some embodiments, the hooks may be integrally made, e.g., cast or machined as a single piece, with the linkage arm 502.

Latch system 500 may be connected to valves 322 and 320. For example, in one embodiment, latch system 500 may include a sensor (e.g., transducer) for determining when lid 316 is in a closed position, e.g., arm 350A latched by hook 352A. In response to the lid 316 being in the closed position, a signal may be sent to motors 512A and 512B to close valves 322 and 320. When the sensor determines that lid 316 is not engaged or locked, a different signal may be sent, in some embodiments, to motors 512A and 512B to open valves 322 and 320.

In other embodiments, the latch system may have merely a mechanical connection to valves 320 and 322. In these embodiments, when one or more of hooks 352A and 352B engages lid 316, valves 320 and 322 may be mechanically closed by portions of system 500. For example, feature 351A (FIGS. 17A and 17B) may be pushed down by arm 352A when lid 316 is being closed. It may be the pushing down of feature 351A that causes one or more of valves 320 and/or 322 to close. In some embodiments, the valves may remain closed even if lid 316 is unengaged. These are merely some examples of components and mechanisms that may be incorporated into a latch system. In other embodiments, a latch system may include additional features including electronic components (e.g., sensors, processors, etc.).

Figure 19A:
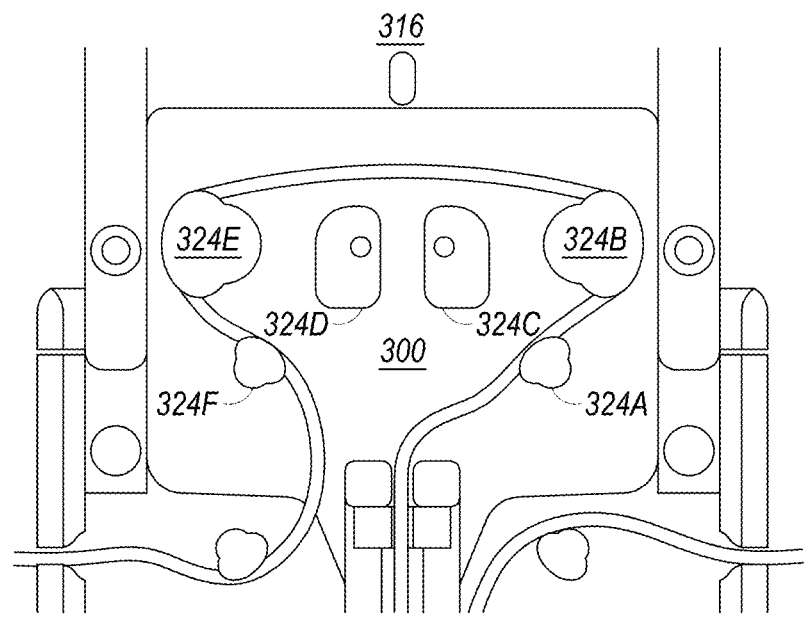
FIGS. 19A and 19B illustrate use of guide posts spaced so that they may be used to route tubing of a bag system in different patterns according to an embodiment.
Figure 19B:
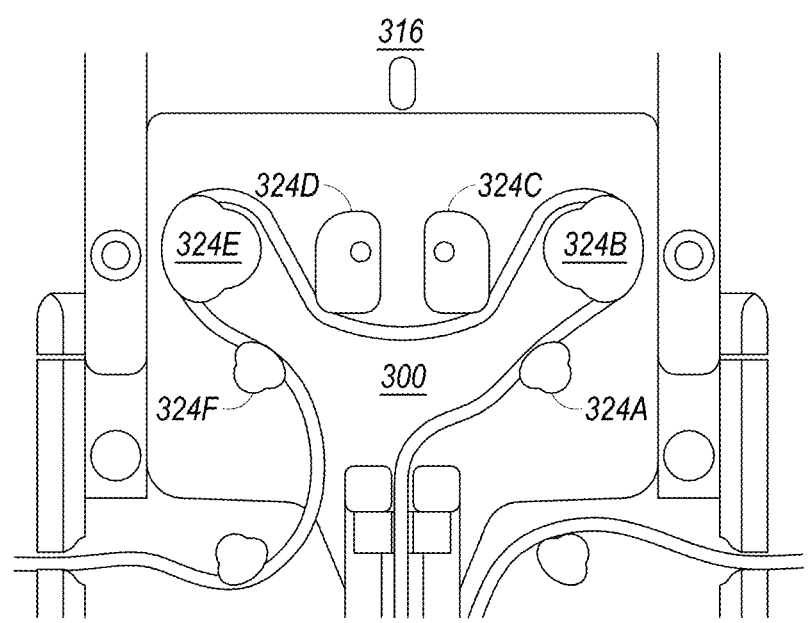

FIGS. 19A and 19B illustrate a number of guide posts 324A-F that may be used to route tubing of a bag system according to an embodiment. Guide posts 324A-F may be part of system box 300. As shown in FIGS. 19A and 19B one feature of the guide posts is that they are spaced apart in a way that allows tubing to be routed in several patterns. FIG. 19A illustrates one possible routing embodiment that may be used when the tubing length is relatively short. FIG. 19B illustrates a second possible routing embodiment that may be used when the tubing length is longer.

Guide posts 324A-F may be used to route tubing in a variety of different patterns. This allows bag systems with different tubing lengths to be used with system box 300. As may be appreciated, without guide posts 324A-F, bag systems with longer tubing may not be able to be used with system box 300 because there may not be a way to position the extra tubing so that it does not interfere with operation of system box 300, e.g., closing of lid 316, kinking of tubing, etc.

In the embodiments shown in FIGS. 19A and 19B, at least some of the guide posts have a lip (325B and 325E) that creates a channel for positioning the tubing. The lip may allow the tubing to fit snuggly around the guide posts to prevent the tubing from moving during separation. In embodiments, the lip may be symmetrical around the post. In other embodiments, as shown in FIGS. 19A and 19B the lip (e.g., 325B and 325E) may be asymmetrical and extend different lengths in different locations.

Figure 20:
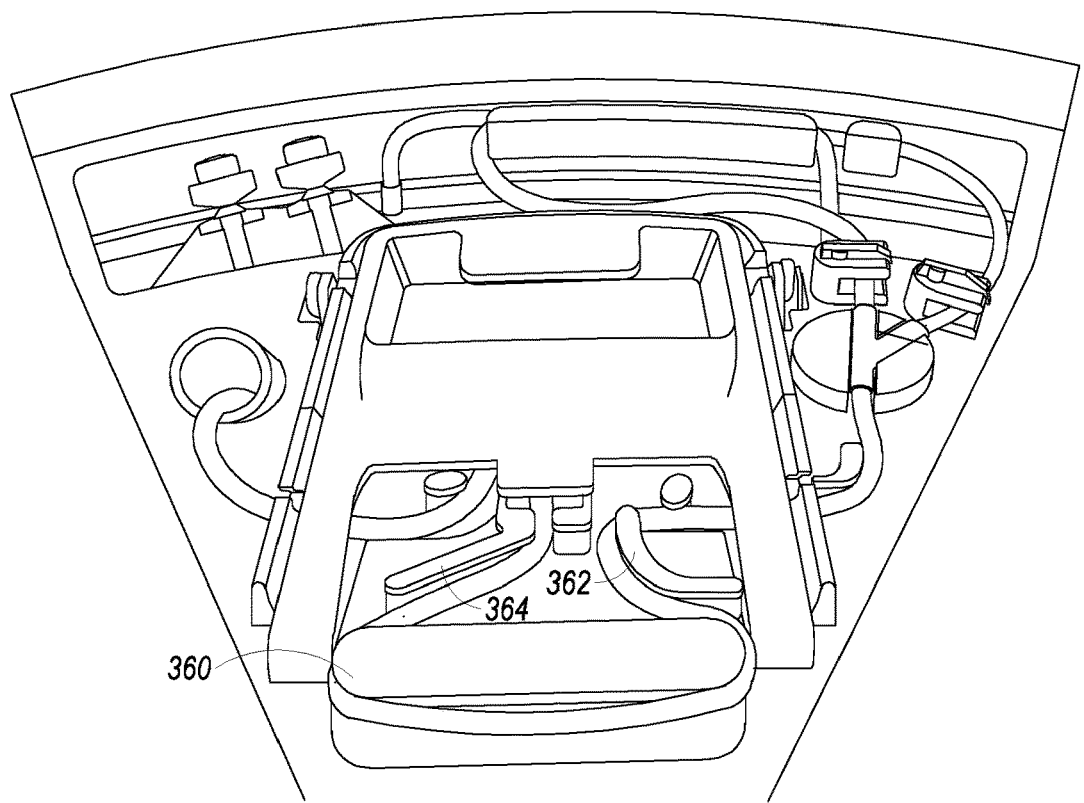
FIG. 20 illustrates a different embodiment of guide posts.

As can be appreciated, other guide posts spacing or patterns may be used in different embodiments. FIG. 20 illustrates another example of some guide posts with channels that may be used in some embodiments. Guide posts 360, 362, and 364 are used to route tubing from a bag system. As shown in FIG. 20, guides posts 360, 362, and 364 include channels where tubing may be positioned and held in place during separation.

Figure 21:
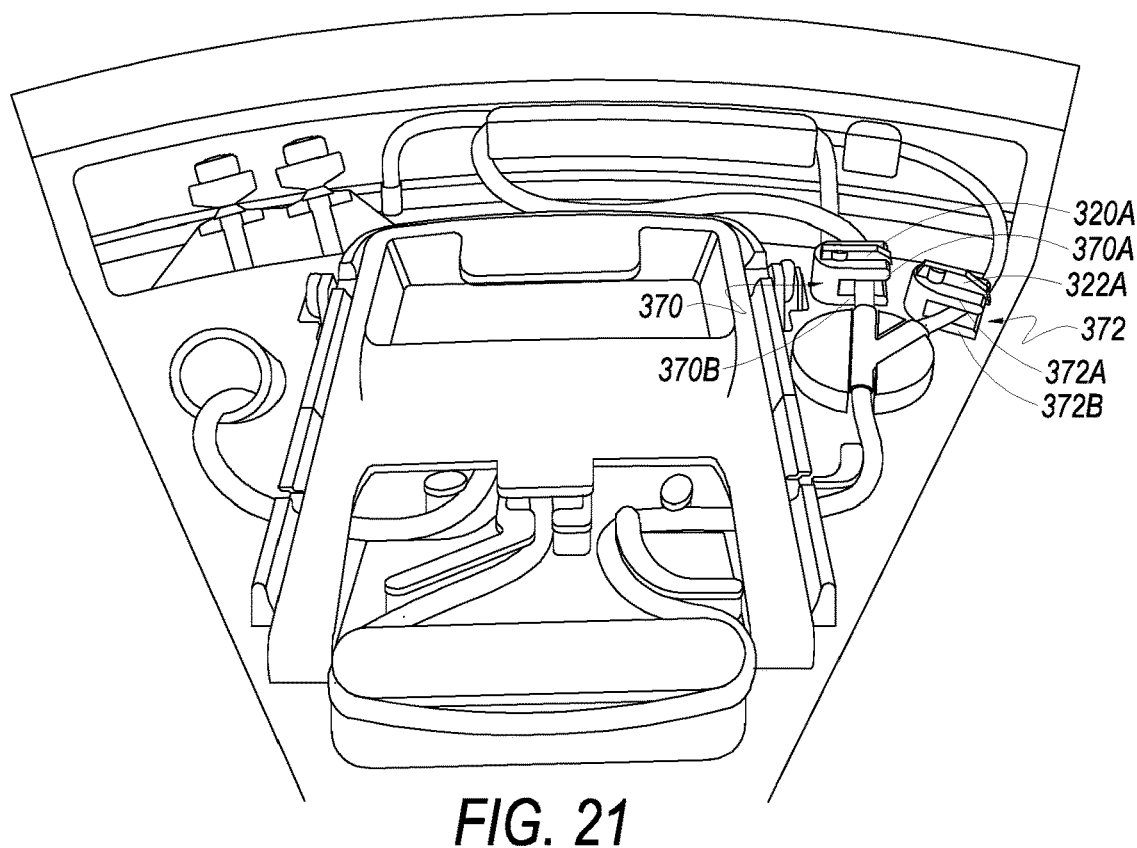
FIG. 21 illustrates a closer view of valves with guide members according to some embodiments.

Referring now to FIG. 21, some embodiments of system box 300 may include guide members that may be used to help keep tubing secured in valves 320 and 322. FIG. 21 shows a close-up view of guide members 370 and 372. Each guide member includes two prongs 370A/370B and 372A/372B. As shown in FIG. 21, jaw 320A of valve 320 is positioned between prong 370A and prong 370B. Similarly, jaw 322A of valve 322 is positioned between prong 372A and prong 372B. Guide members 370 and 372 help to keep tubing positioned under jaws 320A and 322A. In some embodiments, the guide members may have other features such as ridges or other feature that provides some friction to maintain tubing positioned in valves 320 and 322.

Figure 22:
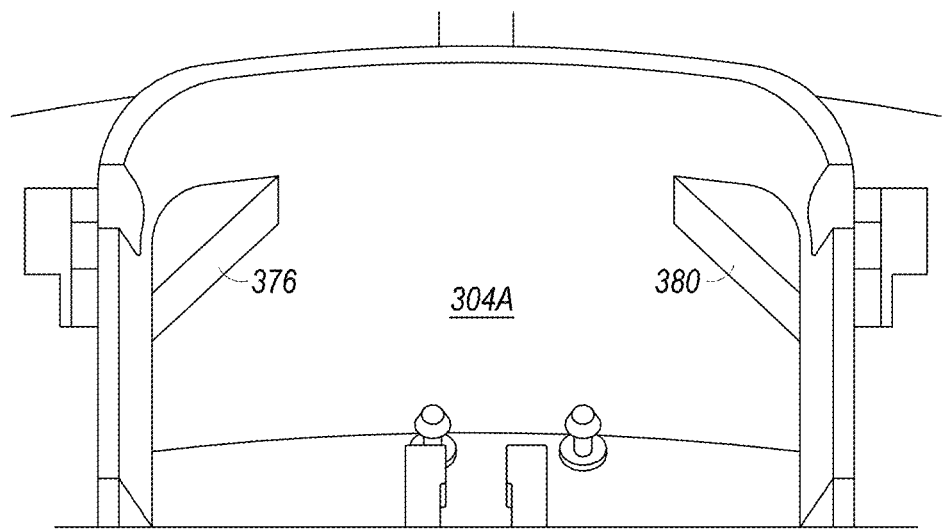
FIG. 22 illustrates features of a chamber that may be incorporated into embodiments of a system box.

FIG. 22 illustrates features of a chamber that may be incorporated into embodiments of a system box. As shown in FIG. 22, chamber 304A includes overhang 376 and overhang 380 that are designed to be positioned above a bag, e.g., bag 302 (FIG. 4) when the bag is in chamber 304A. As can be appreciated, in some embodiments where a bag of composite liquid is placed inside chamber 304A and is subjected to a centrifugal field, some portions of the bag may extend (e.g., expand), which may stretch the bag during centrifugation. This stretching may cause some other location of the bag to collapse, making removal of all of the components from the bag after separation more difficult. Overhang 376 and overhang 380 provide support to some of the top portions of the bag in chamber 304A to prevent expansion or stretching of the bag when it is subjected to a centrifugal field.

It is noted that overhangs 376 and 380 are provided for illustration only. Other embodiments may provide other features that function to support a bag in chamber 304A and prevent extension of a bag during centrifugation. For example, embodiments may provide for additional curved surfaces at the bottom or sides of chamber 304A. Additionally, projections from the side wall of chamber 304A may be located in particular locations, corners, edges, sides, etc. where it may be useful to support a bag in chamber 304A to avoid extension of the bag.

Figure 23:
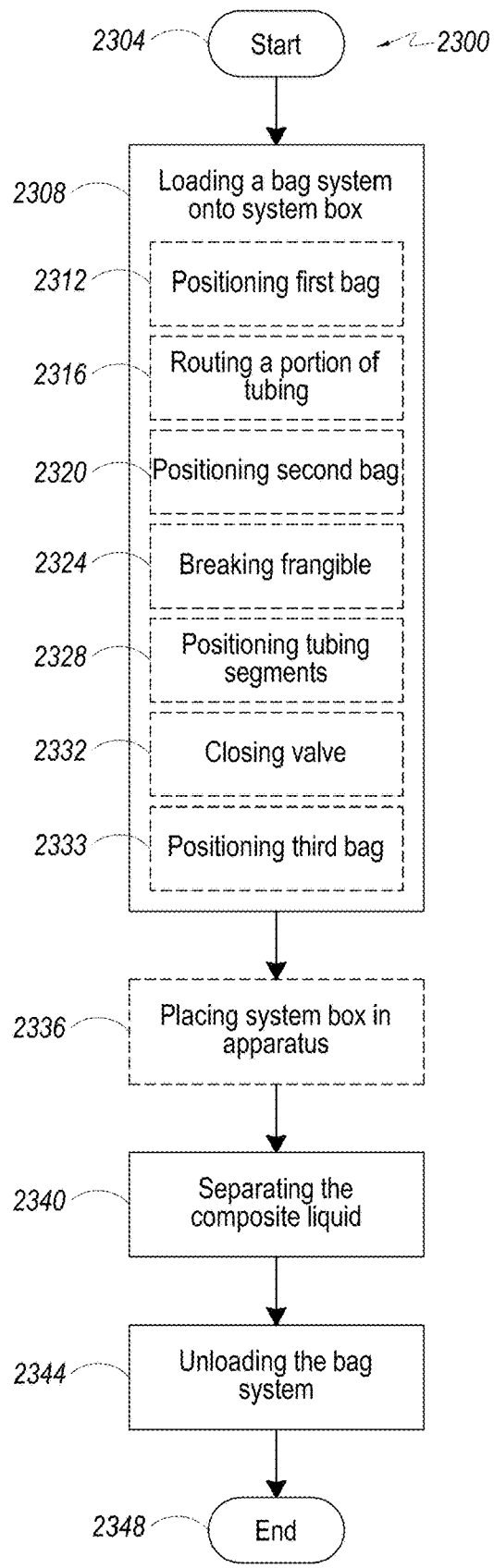
FIG. 23 illustrates a flow chart of a method for separating components from a composite liquid.

FIG. 23 illustrates a flow chart 2300 for a process of separating components from a composite liquid. In one embodiment, the composite liquid may be whole blood, and the components may be one or more of plasma, platelets, white blood cells, buffy coat, red blood cells, and combinations thereof. Although the steps in flow chart 2300 may be described below as performed by an operator, machines, or other apparatus, embodiments are not limited thereto. For example, some steps may be described as performed by an operator, while others are performed by one or more features of a system box or a separation apparatus (e.g., a centrifuge apparatus). This is done merely for illustrative purposes, and flow chart 2300 is not limited to being performed in a specific way, e.g., by any specific device, feature, or component.

Flow 2300 starts at 2304. At step 2308, a bag system may be loaded onto a system box. The system box may be an embodiment of system box 300 shown and described above with respect to FIGS. 3-10. The bag system may also be any suitable bag system that includes one or more bags, with one bag containing the composite liquid. In one embodiment, the bag system may be a whole blood bag system that is used to collect whole blood, separate whole blood into components, store separated components, and utilize the components in patients. An example of a bag system is system 10 described above with respect to FIG. 1.

As shown in FIG. 23, step 2308 may include a number of sub-steps. Some sub-steps are shown and described in FIG. 23, however, other steps (not shown) may be performed in other embodiments, e.g., positioning tubing in valves for clamping. Further, the sub-steps may be performed in any order or in parallel.

At sub-step 2312, a first bag of the bag system is positioned in a first chamber of the system box. The first bag may comprise the composite liquid, for example whole blood. In other embodiments, the first bag may be a bag in which one of the components, e.g., plasma, may be stored after separation. At sub-step 2316 a portion of tubing that connects the first bag to a second bag of the bag system may be routed in the system box. Sub-step 2316 may involve routing the tubing around guide posts (e.g., 324A-F or 360, 362, and 364). In some embodiments, the guide posts may be positioned to allow the tubing to be routed in different ways to accommodate different tubing lengths. For example, the system box may have guide posts such as posts 324A-F shown in FIGS. 3-10. As described above, the guide posts 324A-F allow different lengths of tubing to be accommodated in the system box.

In some embodiments, sub-step 2316 may involve positioning a portion of tubing in a tubing path. In some embodiments, the tubing path may be located to allow one of the bags, e.g., the second bag of the bag system, to be filled with a component separated from the composite liquid while pushing air out of the bag. As one example, the tubing path may be located so that when the system box is subjected to a centrifugal field, a portion of tubing is positioned in a higher force region, than an inlet port of the bag being filled with the component. This may allow the bag to be filled with a component while air is pushed out of the bag. One example of this embodiment is illustrated in FIG. 16. As described above, the portion 342 of the tubing path positions tubing in a higher force region than inlet port 346, pushing air out of the bag and allowing, e.g., plasma, to fill the bag and the tubing up to valve 322.

In yet other embodiments, sub-step 2316 may also include positioning a portion of tubing adjacent a sensor to sense as components flow through the portion of tubing. For example, a sensor, such as sensor 330, may be in a channel (e.g., channel 336) of the system box. Sub-step 2316 may include positioning a portion of tubing in the channel adjacent sensor 330, which may sense as components such as plasma, platelets, white blood cells, and/or red blood cells flow through the tubing.

At sub-step 2320, a second bag is positioned in a second chamber of the system box. Flow 2300 then passes to sub-step 2324 where a frangible is broken to open fluid communication between the first bag and the second bag. The frangible may be broken by closing a lid that includes a frangible breaking mechanism. In one embodiment, the frangible breaking mechanism may be a ridge, e.g., ridge 326 on an interior surface 316A of lid 316 of system box 300.

As may be understood, sub-step 2324 may be preceded by a step or sub-step in which a frangible is placed in a channel of the system box in a position to be broken. As one example, sub-step 2316 may further involve positioning a frangible in a channel above an opening of a recess. At sub-step 2324, a frangible breaking mechanism, e.g., ridge 326 (which may be on a lid), may push against the frangible, deflecting the frangible into the opening of the recess and breaking the frangible, creating open fluid communication between the first bag and second bag.

In some embodiments, there may be more than one frangible breaking sub-step that utilizes different structures and methods of breaking a frangible. For example, in addition to the frangible breaking sub-step 2316, a frangible may be broken to open communication with a bag containing preservative solution, which may be performed after other sub-steps. The frangible may be broken using a different opener, for example, such as one provided adjacent a chamber for holding the bag of preservative solution, e.g., opener 349 (FIG. 16). The additional frangible breaking steps may be performed before, after, or in parallel with sub-step 2324.

At sub-step 2328, sealed tubing segments may be placed in a tubing holder. In some embodiments, each segment of tubing may hold a volume of composite liquid, e.g., whole blood. The tubing segments may be used as samples that provide information about the composite fluid, e.g., concentration of a component and/or provide an indication of the quality of the separation after components have been separated from the composite fluid. The sealed tubing segments may be formed by heating and melting portions of tubing that contain the composite liquid, e.g., blood, creating sealed segments of tubing with a volume of composite liquid. The tubing segments may be folded and placed in a tubing holder, e.g., tubing holder 318.

At sub-step 2332, a valve may be closed. In some embodiments, sub-step 2332 and 2328 may be performed substantially simultaneously. For example, in one embodiment, by closing a lid over the first chamber, the frangible may be broken (2328) and a valve may be closed (2332). As noted above, a system box may include a latch system that provides for closing a valve. Latch system 500 described above, provides, in embodiments, for closing one or more of valves 320 and 322 when lid 316 engages one or more hooks 352A and/or 352B.

Additionally, closing of the lid to both close a valve and break a frangible may also accomplish other functions. For example, in embodiments, when the lid is closed, the first bag may be completely surrounded to ensure that during separation the bag is not extended.

Sub-step 2333 may be performed to position a third bag in a third chamber of the system box. The bag may be a bag for holding a component after separation. In other embodiments, the bag may be a bag with preservative solution that is added to a component for storage.

Flow passes from step 2333, and its various sub-steps, to optional step 2336 where the system box is placed in a separation apparatus. In embodiments, the separation apparatus may be a centrifuge apparatus, such as apparatus 200 described above with respect to FIG. 2. It is noted that several system boxes loaded with bag systems may be placed in the apparatus at the same time. In embodiments, the system box may already be positioned in the apparatus before step 2308 in which case optional step 2336 may not be performed as part of flow 2300. For example, an apparatus may have a plurality of system boxes pre-installed. In these embodiments, step 2308 may not be part of the process of separating components from a composite liquid but rather be performed before flow 2300 starts.

At step 2340 the composite liquid in the first bag may be separated by the separation apparatus. The separation may be accomplished in any suitable way, some non-limiting examples including centrifugation, acoustic separation, gravity separation, etc. In one embodiment, a centrifuge apparatus, such as apparatus 200 is used to separate the composite liquid into components. For example, whole blood may be separated into plasma, a buffy coat (platelets and white blood cells), and red blood cells.

In those embodiments in which step 2340 is performed, at least in part by a centrifuge apparatus, the system box, the bag system, and the composite liquid may be subjected to a centrifugal field, which may be generated by spinning the system box and the bag system loaded on the system box around an axis of rotation. For example, the system box may be installed in a centrifugal drum 208 of apparatus 200 (FIG. 2). Apparatus 200 may then spin subjecting the centrifugal drum 208, the system box, the bag system, and the composite liquid to a centrifugal field.

At step 2344 the bag system may be unloaded from the system box. The bag system may be unloaded from the system box, while the system box remains in the separation apparatus. In other embodiments, prior to removing the bag system from the system box, the system box may be removed from the separation apparatus. Flow 2300 then ends at 2348.

Although flow 2300 has been described with steps listed in a particular order, the present disclosure is not limited thereto. In other embodiments, steps may be performed in different order, in parallel, or any different number of times, e.g., before and after another step. Also, as indicated above, flow 2300 includes some optional steps/sub-steps. However, those steps above that are not indicated as optional should not be considered as essential to the invention, but may be performed in some embodiments of the present invention and not in others.

It will be apparent to those skilled in the art that various modifications and variations can be made to the methods and structure of the present invention without departing from its scope. Thus it should be understood that the invention is not limited to the specific embodiments or examples given. Rather, the invention is intended to cover modifications and variations.

While example embodiments and applications of the present invention have been illustrated and described, it is to be understood that the invention is not limited to the precise configuration described above. Various modifications, changes, and variations apparent to those skilled in the art may be made in the arrangement, operation, and details of the methods and systems of the present invention.

What is claimed is:

1. A system box for holding a bag system, the system box comprising:
    a first chamber comprising a first opening;
    a second chamber comprising a second opening;
    a lid movable from an open position to a closed position, the lid comprising an interior surface and an exterior surface, wherein when the lid is in the closed position the interior surface covers at least a portion of the first opening;
    a first ridge on the inside surface of the lid; and
    a recess, wherein when the lid is in the closed position the first ridge is positioned above the recess;
    at least one outer wall; and
    a tubing holder adjacent the first chamber, wherein the tubing holder is positioned at an angle so that a distal end of the tubing holder is closer to the outer wall than a proximal end of the tubing holder.

2. The system box of claim 1, wherein the least one outer wall is curved.

3. The system box of claim 2, wherein a top portion of the outer wall comprises a liquid guard.

4. The system box of claim 3, wherein the liquid guard curves toward the first chamber.

5. The system box of claim 3, wherein the liquid guard extends above the lid when the lid is in the closed position.

6. The system box of claim 1, wherein at least a portion of the second chamber is between the first chamber and the outer wall.

7. The system box of claim 6, further comprising:
    a third chamber, wherein at least a portion of the third chamber is between the first chamber and the outer wall.

8. The system box of claim 7, further comprising:
    a tubing path for routing a portion of tubing connecting a first bag of the bag system with a second bag of the bag system.

9. The system box of claim 8, wherein at least a portion of the tubing path is between the outer wall and the first chamber.

10. The system box of claim 8, wherein at least a portion of the tubing path is between the outer wall and the second chamber.

11. The system box of claim 10, wherein the portion of the tubing path comprises a ledge on which the tubing is placed.

12. The system box of claim 1, further comprising:
    a plurality of guide posts adjacent the first chamber.

13. The system box of claim 12, further comprising:
    wherein at least a portion of the plurality of guide posts comprise a lip.

14. The system box of claim 13, wherein the plurality of guide posts are spaced to allow tubing from the bag system to be wrapped around the guide posts in a plurality of patterns.

15. A system box for holding a bag system, the system box comprising:
    a first chamber comprising a first opening;
    a second chamber comprising a second opening;
    a lid movable from an open position to a closed position, the lid comprising an interior surface and an exterior surface, wherein when the lid is in the closed position the interior surface covers at least a portion of the first opening, wherein the lid further comprises a first arm and a second arm;
    a first ridge on the inside surface of the lid;
    a recess, wherein when the lid is in the closed position the first ridge is positioned above the recess;
    a latch system with a first hook for engaging the first arm of the lid and a second hook for engaging the second arm of the lid;
    a first guide member, wherein a jaw of a first valve is positioned between two prongs of the first guide member;
    a second guide member, wherein a jaw of a second valve is positioned between two prongs of the second guide member; and
    wherein the first valve is connected to the latch system, so that when the lid engages at least one of the first hook or the second hook, the first valve is closed.

16. The system box of claim 15, further comprising:
    the second valve connected to the latch system, so that when the lid engages at least one of the first hook or the second hook, the second valve is closed.

17. The system box of claim 15, further comprising:
    a plurality of guide posts adjacent the first chamber.

18. The system box of claim 17, further comprising:
    wherein at least a portion of the plurality of guide posts comprise a lip.

19. The system box of claim 18, wherein the plurality of guide posts are spaced to allow tubing from the bag system to be wrapped around the guide posts in a plurality of patterns.

* * * * *